United States Patent
Natrajan et al.

(10) Patent No.: US 7,875,467 B2
(45) Date of Patent: Jan. 25, 2011

(54) APPLICATIONS OF ACRIDINIUM COMPOUNDS AND DERIVATIVES IN HOMOGENEOUS ASSAYS

(75) Inventors: Anand A. Natrajan, Manchester, NH (US); Todd Sells, Bellingham, MA (US); Hartmut Schroeder, Franklin, MA (US); Guohan Yang, Mansfield, MA (US); David Sharpe, Foxborough, MA (US); Qingping Jiang, East Walpole, MA (US); Hana Lukinsky, Portland, OR (US); Say-Jong Law, Westwood, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 361 days.

(21) Appl. No.: 11/944,131

(22) Filed: Nov. 21, 2007

(65) Prior Publication Data

US 2008/0305557 A1 Dec. 11, 2008

Related U.S. Application Data

(62) Division of application No. 10/260,504, filed on Sep. 27, 2002, now Pat. No. 7,319,041.

(51) Int. Cl.
*G01N 33/533* (2006.01)
*G01N 33/536* (2006.01)
*G01N 33/53* (2006.01)
*C07D 219/08* (2006.01)

(52) U.S. Cl. ........................ 436/546; 436/536; 436/800; 435/7.1; 435/7.93; 435/968; 546/104

(58) Field of Classification Search ...................... None
See application file for complete search history.

(56) References Cited

U.S. PATENT DOCUMENTS 5,468,646 A * 11/1995 Mattingly et al. ........... 436/501
5,593,845 A * 1/1997 Akhavan-Tafti et al. ...... 435/7.9

FOREIGN PATENT DOCUMENTS

WO WO 98/02421 * 1/1998

* cited by examiner

*Primary Examiner*—Shafiqul Haq

(57) ABSTRACT

Chemiluminescent acridinium compounds are used in homogeneous assays to determine the concentration of an analyte in a sample without strong acid or strong base treatment. The chemiluminescent acridinium compounds include acridinium esters with electron donating functional groups at the C2 and/or C7 position on the acridinium nucleus to inhibit pseudo-base formation, or acridinium sulfonamides with or without electron donating functional groups at the C2 and/or C7 position on the acridinium nucleus.

11 Claims, 10 Drawing Sheets ized. The dentral<br>
APPLICATIONS OF ACRIDINIUM COMPOUNDS AND DERIVATIVES IN HOMOGENEOUS ASSAYS This application is a divisional of application Ser. No. 10/260,504 filed Sep. 27, 2002, the contents of which are hereby incorporated by reference in their entirety.

BACKGROUND OF THE INVENTION

1. Field of the Invention

The present invention relates to the application of acridinium compounds with certain specific structural features in homogeneous assays. Important structural features that are necessary, to ensure light emission at mild pH are disclosed herein.

2. Background of the Invention

Chemiluminescent acridinium esters (AE) are extremely useful labels that have been used extensively in immunoassays and nucleic acid assays. U.S. Pat. Nos. 4,745,181; 4,918, 192; 5,110,932; 5,241,070; 5,538,901; 5,663,074 and 5,656, 426 disclose a variety of stable acridinium esters with different functional groups for conjugation to a variety of biologically active molecules referred to as analytes.

U.S. Pat. No. 5,656,426 discloses a hydrophilic acridinium ester with increased quantum yield. Considerable effort has also been directed towards the design of acridinium esters whose emission wavelength can be altered by either incorporating unique structural features in the acridinium ester or by employing the principle of energy transfer. See U.S. Pat. Nos. 5,395,752; 5,702,887; 5,879,894; 6,165,800; and 6,355,803.

Acridinium sulfonamides are another class of chemiluminescent compounds where the substituted phenolic leaving group is replaced with a substituted sulfonamide. The synthesis and applications of these acridinium compounds in heterogeneous assays have been described in the prior art: Adamczyk et al, *Tetrahedron*, vol. 55, pages 10899-10914 (1999); Mattingly, *J. Biolumin. Chemilumin.*, vol. 6, pages 107-114 (1991); and Adamcyzk et al, *Bioconjugate Chem.* vol. 11, pages 714-724 (2000).

Mechanistically, acid treatment converts the pseudo-base form of the acridinium compound to the acridinium ester which can then participate in the chemiluminescent reaction with hydrogen peroxide. The addition of alkali serves not only to neutralize the acid but also to raise the pH of the reaction medium for the ionization of hydrogen peroxide.

The relatively harsh reagents with strong acidic pHs on the order of Less than 2 and strong basic pHs on the order of greater than 12 that are required for triggering chemiluminescence as described above are detrimental to the preservation of binding complexes such as antibody-hapten complexes or nucleic acid hybrids. This is not a problem in a heterogeneous assay format where signal generation is typically performed at the end of the assay and unbound tracer and/or interfering substances have been removed.

A homogeneous assay is an analytical method where measurement of a substance of interest is performed without any separation procedures. In a homogeneous assay format, in order to detect the occurrence of binding events using chemiluminescent acridinium compounds as tags, light generation must occur under milder pH conditions because harsh pH conditions are detrimental to the preservation of binding complexes. Additionally, a mechanism to distinguish between bound and unbound tracer or analyte is needed because no separation is performed in a homogeneous assay. These constraints have hampered the utility of acridinium compounds in homogeneous assays.

The only homogeneous assays using acridinium compounds that are believed to have been described in the literature are "hybridization protection assays". See Nelson et al, *Biochemistry* vol. 35, pages 8429-8438 (1996). In these assays, the acridinium ester portion of an acridinium ester-labeled nucleic acid probe is selectively decomposed by hydrolysis when it is not hybridized to a target. Hybridization of the probe to its target results in protection of the acridinium ester from hydrolysis thereby enabling the distinction between hybridized versus non-hybridized DNA. By employing acridinium esters with similar hydrolysis rates but different time-dependent light emission profiles, homogeneous multi-analyte assays were devised to detect nucleic acids.

In Nelson et al., the structure of the acridinium ester is not being altered to enable light emission under mild conditions. Rather, the Nelson et al. assay takes advantage of the different rates of hydrolysis (degradation) of the acridinium ester when a nucleic acid labeled with the acridinium ester is either free or is hybridized to the complementary sequence of the acridinium ester-labeled nucleic acid. Thus, the property of the nucleic acid, whether or not it is hybridized to its complementary sequence, is being used to alter the rate of degradation of the acridinium ester.

Fluorescence Resonance Energy Transfer (FRET) is a well-known phenomenon that has been widely used to study proximity effects in biomolecules. In FRET, an electronically excited fluorescent donor molecule transfers its electronic energy to a second, acceptor molecule through dipole-dipole coupling. This energy transfer causes fluorescence quenching of the donor. If the acceptor is fluorescent, its fluorescence is then observed.

The efficiency of energy transfer is inversely proportional to the sixth power of the distance separating the donor and acceptor fluors and also depends directly on the fluorescent quantum yield of the donor and the extinction coefficient of the acceptor at the wavelength of maximal emission of the donor. Because of the distance dependence, FRET is normally not observed at distances >10 nm.

Homogeneous immunoassays based on chemiluminescence energy transfer have also been described using isoluminol as the chemiluminescent donor and fluorescein as the acceptor. See Patel et al, *Clin. Chem.* vol. 29/9, pages 1604-1608 (1983). Assays for small analytes such as progesterone as well as protein antigens were constructed using the isoluminol-fluorescein, donor-acceptor pair presumably because chemiluminescence from isoluminol can be triggered under mild conditions.

BRIEF DESCRIPTION OF THE DRAWINGS

FIG. 1 depicts pH titrations of dimethyl acridinium ester (DMAE);

FIG. 2 depicts pH titrations of 2,7-dimethoxy-DMAE;

FIG. 3 depicts a homogeneous carbamazepine assay using an acridinium ester tracer;

FIG. 4 depicts a homogeneous carbamazepine assay using an acridinium sulfonamide tracer;

FIG. 5 depicts a homogeneous theophylline assay using an acridinium ester tracer;

FIG. 6 depicts a homogeneous theophylline assay using an acridinium sulfonamide tracer;

FIG. 7 depicts a homogeneous valproate assay using an acridinium ester tracer;

FIG. 8 depicts a homogeneous valproate assay using an acridinium sulfonamide tracer;

FIG. 9 depicts a homogeneous valproate assay using quenching;

FIG. 10 depicts a CL RET from Biotin-AE to Biotin-jfNpFL in a streptavidin complex.

DESCRIPTION OF THE PREFERRED EMBODIMENTS

Figure 1:
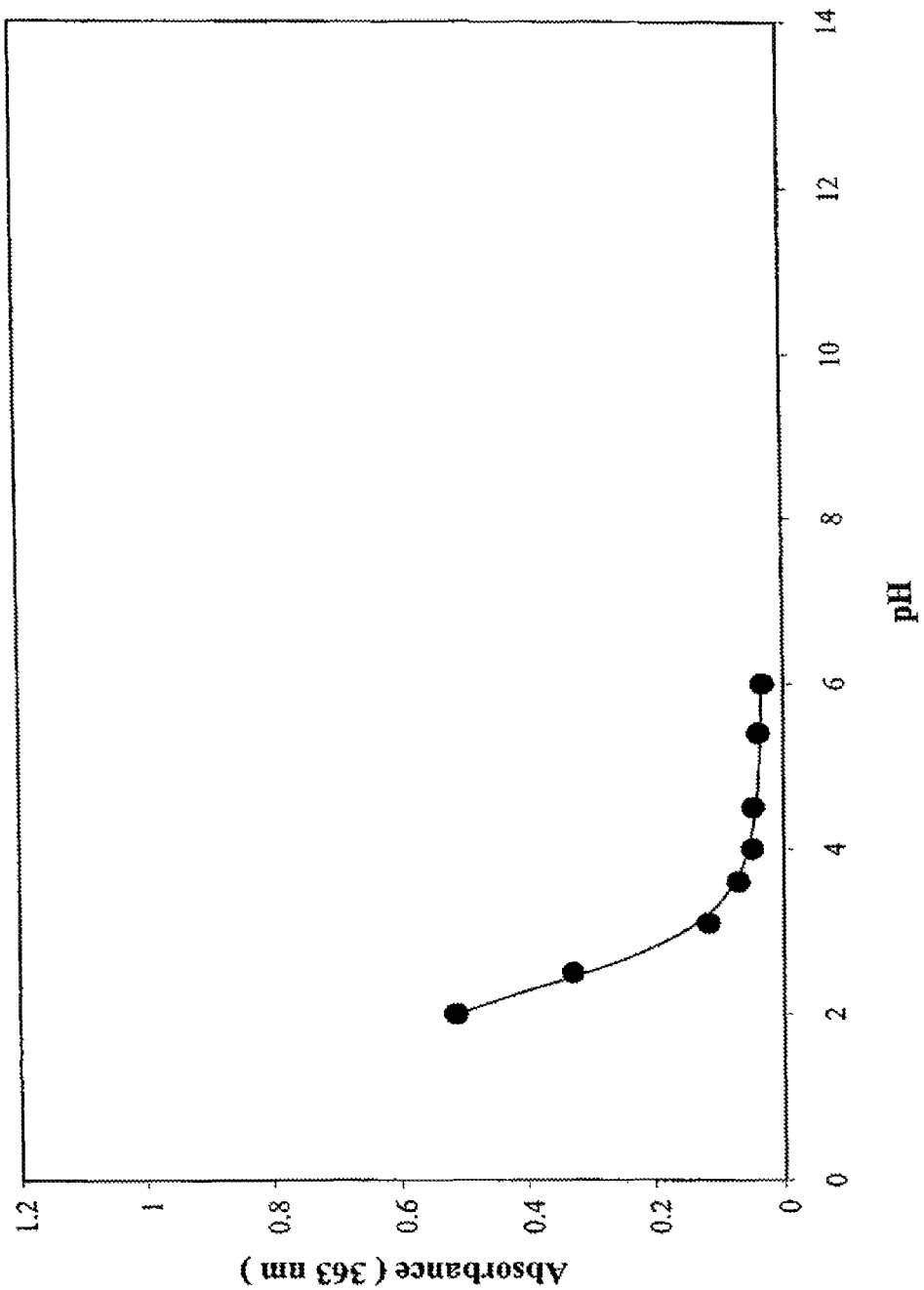
FIGS. 1 to 10 are all graphical representations.

This invention comprises certain acridinium compounds including acridinium esters and acridinium sulfonamides whose chemiluminescence can be triggered under relatively mild pH conditions. The availability of such acridinium compounds whose chemiluminescence can be triggered under relatively mild conditions makes it possible to use such compounds in homogeneous resonance energy transfer assays. It has been unexpectedly discovered, that hapten tracers derived from these acridinium compounds show significant differences in their efficiency of light production depending upon whether they are free in solution or bound to their respective antibodies. The discovery of this phenomenon has enabled the production of homogeneous assays for clinically important analytes.

Hapten tracers derived from the inventive acridinium compounds upon binding to their corresponding antibodies exhibit an alteration in the efficiency of light emission. Efficiency of light emission means that the acridinium compounds emit more light or less light depending upon whether they are free or are bound to antibodies. For acridinium esters, light emission is increased whereas for acridinium sulfonamides, light emission is decreased when these compounds are bound to antibodies. Therefore, depending upon the acridinium compound, light emission is either enhanced or attenuated.

These effects have been utilized to devise homogeneous assays for determining the concentration or quantitation or detection of such clinically important analytes, including theophylline, valproate and carbamazepine. In addition the acridinium compounds disclosed herein can also be used in resonance energy transfer (RET) assays where excited state energy from the acridone formed from the acridinium compound during the chemiluminescent reaction is transferred in an intermolecular fashion to an acceptor molecule such as naphthofluorescein and dabsyl whose spectral properties (emission at a different wavelength or quenching) are distinguishable from that of the acridinium compound.

Acridinium Structure and Pseudo-Base Formation

It is well known that acridinium compounds exist in an equilibrium between the acridinium form and the pseudo-base form in aqueous media where virtually all immunoassays are performed. The pseudo-base form of acridinium compounds cannot react with hydrogen peroxide and thus cannot produce chemiluminescence. The equilibrium between the chemiluminescent acridinium form and non-chemiluminescent pseudo-base form is strongly influenced by the pH of the medium. Acidic pH promotes the formation of the acridinium form and basic pH promotes the formation of the pseudo-base form. The following equilibrium reaction shows the conversion of the acridinium compound to the pseudo-base:

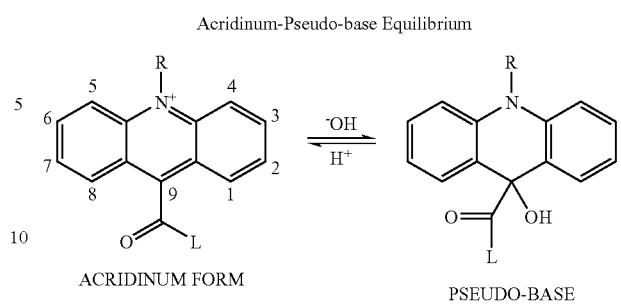

Acridinum-Pseudo-base Equilibrium

ACRIDINUM FORM  PSEUDO-BASE

R is typically an alkyl, alkenyl, alkynyl or aralkyl containing up to 20 heteroatoms; or a sulfopropyl or sulfobutyl group; L is typically a leaving group such as an aromatic alcohol or a sulfonamide In heterogeneous assay formats, chemiluminescence from acridinium compounds or acridinium compound-labeled biologically active molecules, referred to as tracers or conjugates, is normally triggered by the sequential addition of two reagents. An initial treatment of the acridinium compound with a strong acid containing peroxide is necessary to convert the pseudo-base form of acridinium compounds to the acridinium form. The subsequent treatment with alkali solution then neutralizes the acid and raises the pH of the reaction medium for the ionization of hydrogen peroxide to allow light emission to take place.

In a homogeneous assay format, light emission occurs from acridinium compounds under mild conditions, that is, at a mild pH of about 6 to 10, preferably about 7 to 9. The maintenance of the acridinium form without addition of a strong acid to the assay medium is a prerequisite to generate chemiluminescence. Moreover, by omitting the acid-treatment step, the need for adding strong base to neutralize the acid and to trigger the chemiluminescence reaction is also obviated.

It has been unexpectedly discovered that acridinium esters bearing electron donating functional groups at the C-2 and/or C-7 positions on the acridinium nucleus are less prone to pseudo-base formation than unsubstituted acridinium esters at the mild pH.

The chemiluminescent acridinium compounds suitable for use in the present invention have the following structure:

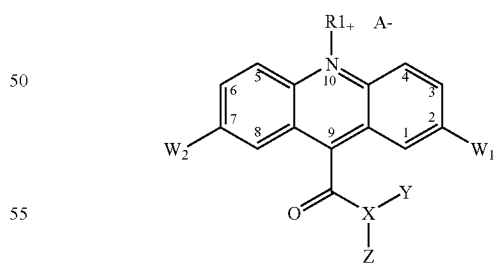

wherein, $R_1$ is an alkyl, alkenyl, alkynyl or aralkyl containing up to 20 heteroatoms; or a sulfopropyl or sulfobutyl group;

X is oxygen or nitrogen;

Y is a branched or straight-chained alkyl containing up to 20 carbon atoms, halogenated or unhalogenated, or a substituted aryl, or heterocyclic ring system; when X is oxygen, Z is omitted and Y is a polysubstituted aryl moiety of the formula:

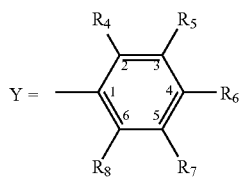

wherein $R_4$ and $R_8$ are the same or different, and are hydrogen, alkyl, alkenyl, alkynyl, alkoxyl (—OR), alkylthiol (—SR), or substituted amino groups that serve to stabilize the —COX— linkage between the acridinium nucleus and the Y moiety, through steric and/or electronic effect;

$R_5$ and $R_7$ are hydrogen or the same as R;

$R_6$=—$R_9$-$R_{10}$, where $R_9$ is not required and is branched or straight-chained alkyl, substituted or unsubstituted aryl or aralkyl containing up to 20 heteroatoms, and $R_{10}$ is a leaving group or an electrophilic functional group attached with a leaving group selected from the group consisting of:

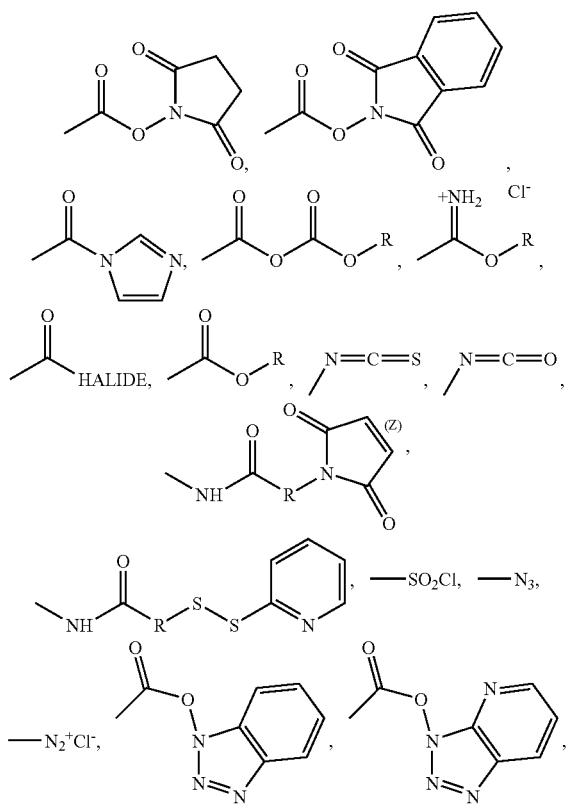

a halide or —COOH;

$R_5$ and $R_6$, and $R_6$ and $R_7$ are interchangeable;

when X is nitrogen, Z is —$SO_2$—Y', and Y' has the same definition of Y and both can be the same or different;

W1 and W2 are the same or different and are electron-donating groups comprising OR, OH, SR, SH, $NH_2$, NR'R";
wherein R, R' and R" can be the same or different, and are selected from the group consisting of alkyl, alkenyl, alkynyl, aryl, and aralkyl containing up to 20 heteroatoms;

$A^-$ is a counter ion which is introduced to pair with the quaternary nitrogen of said acridinium nucleus, and is selected from the group consisting of $CH_3SO_4^-$, $FSO_3^-$, $CF_3SO_4^-$, $C_4F_9SO_4^-$, $CH_3C_6H_4SO_3^-$, halide, $CF_3COO^-$, $CH_3COO^-$, and $NO_3^-$.

More specifically, the acridinium compound can be an acridinium ester of the following structure:

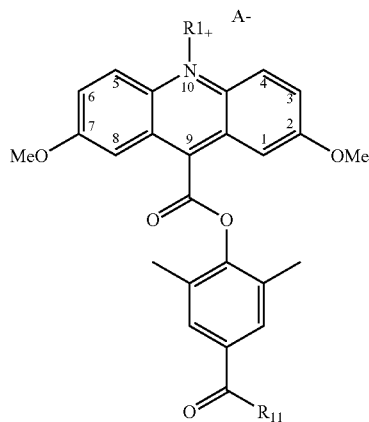

wherein R11 is selected from the following:

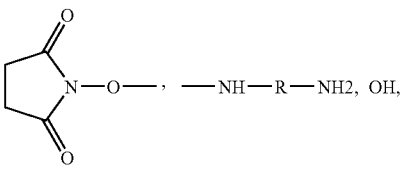

and R1, R and A– are as already described.

Alternatively, the acridinium compound can be an acridinium ester of the following structure:

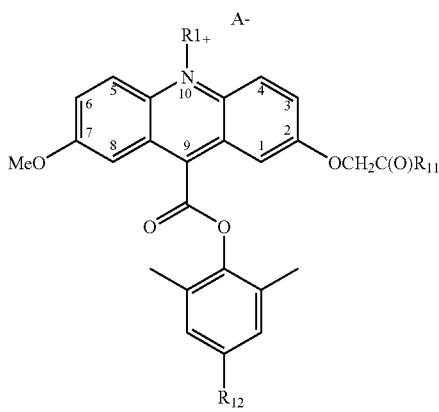

wherein $R_{12}$ is selected from hydrogen, amino, hydroxyl, halide, nitro, —CN, —$SO_3H$, —SCN, —OR, NHCOR, —COR, —COOH, —COOR, or —CONHR; and $R_1$, $A^-$ and $R_{11}$ are as already described.

The acridinium compound of the present invention can also be an acridinium sulfonamide of the following structure:

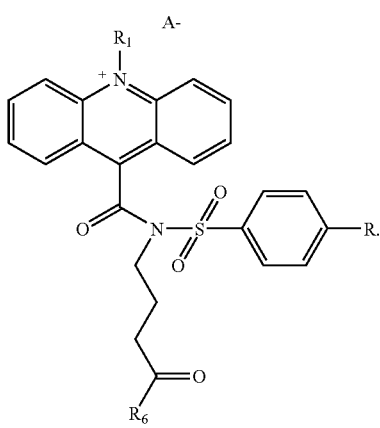

wherein $R_1$, $A-$, R and $R_6$ are as already described.

Figure 2:
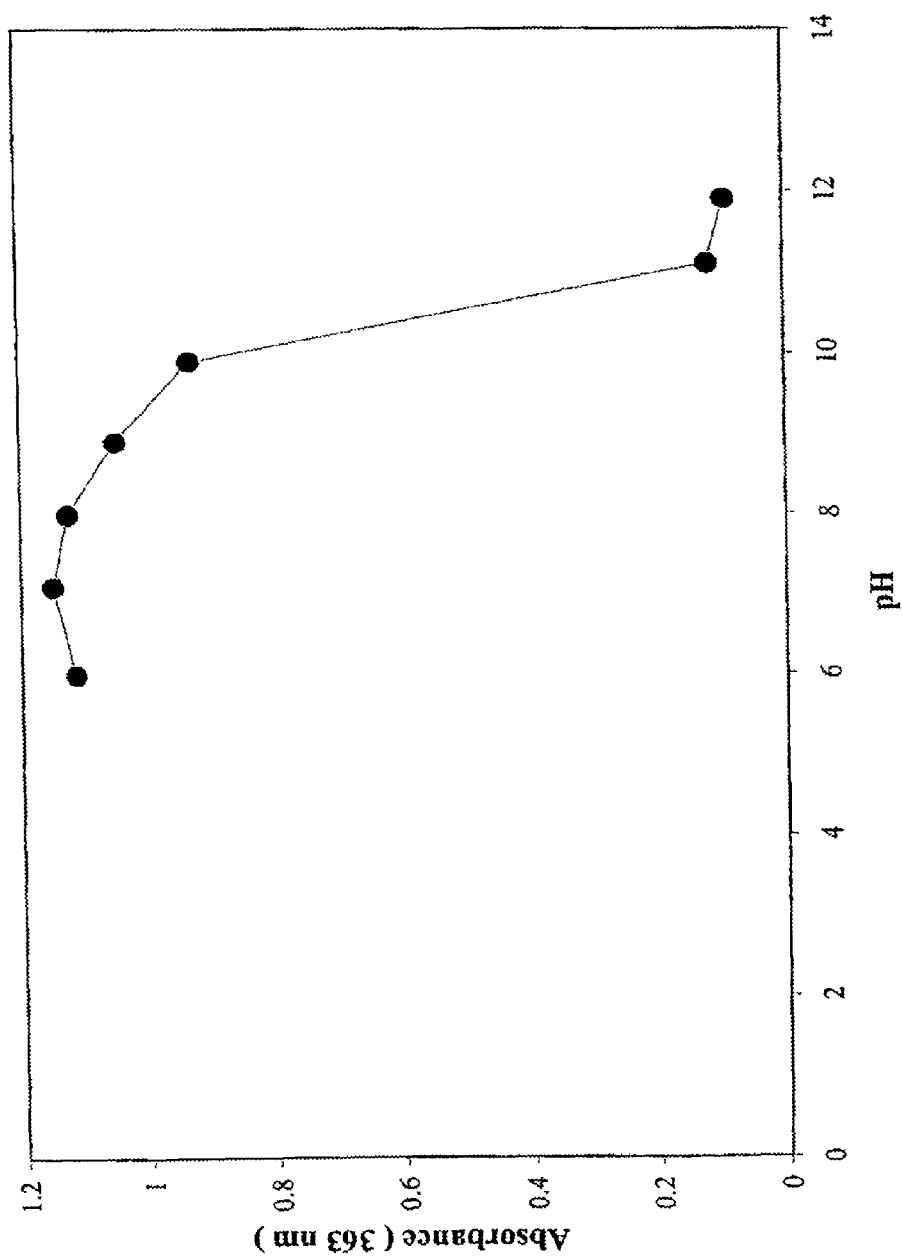

In FIG. 1, pH titrations of dimethyl acridinium ester (DMA) and in FIG. 2, pH titrations of 2,7-dimethoxy-DMAE are shown where the UV-absorption band of the acridinium chromophore is plotted as a function of pH. The decrease in intensity of this absorption band is indicative of the disruption of the acridinium chromophore and the formation of pseudo-base. It is evident from FIG. 1 for DMAE that pseudo-base formation is essentially complete at pH >4. It is evident from FIG. 2 that for the electron-rich, 2,7-dimethoxy analog, pseudo-base formation is complete only at pH >11.

In order to determine whether chemiluminescence from electron-rich acridinium compounds can be triggered without acid pre-treatment and at milder pH, light emission from several acridinium compounds including 2,7-dimethoxy-DMAE, and 2-CME-7-methoxy-DMAE and anti-TSH protein conjugates were measured by employing a single chemical reagent comprising 1% hydrogen peroxide and 0.5% cetyltrimethylammonium chloride (CTAC) surfactant in sodium carbonate buffer either at pH 8.3 or at pH 9.

The results are summarized in Table 1. For all the compounds listed, the amount of light emitted using the modified triggers is expressed as a percentage of the light that is normally measured following the sequential addition of 0.5% hydrogen peroxide in 0.1 N nitric acid followed by 0.25 N NaOH containing the CTAC surfactant. Also included in the table are results for an acridinium sulfonamide. Acridinium sulfonamides are comparable to acridinium esters in their quantum efficiency of light production and hydrolytic stability.

Chemiluminescence was measured for 5 seconds on a Magic Lite Analyzer Luminometer (MLAl, Bayer Diagnostics). Samples of the various compounds were prepared in 10 mM phosphate pH 8 containing 150 mM NaCl, 0.05% BSA and 0.01% sodium azide.

The data in Table 1 indicates that the placement of electron donating functional groups at the C-2 and/or C-7 positions enables the chemiluminescent reaction from the corresponding acridinium ester to occur at a mild pH range of about 8 to 9. The C2 and C7 positions on the acridinium molecule are equivalent. Thus, where there is only one functional group, for example, methoxy or hydroxy, at either of these positions, it would be referred to as being in the C2 position. If there are two functional groups, then the second corresponding position is C7. Because the acridinium molecule is symmetrical, the C2 position is the same as C7. Similarly the C3 position is the same as C6. However, C2 and C3 are not equivalent. Thus a single methoxy group at C2 is not equivalent to a methoxy group at C3.

The chemical structure of the acridinium compounds listed in Table 1 are as follows:

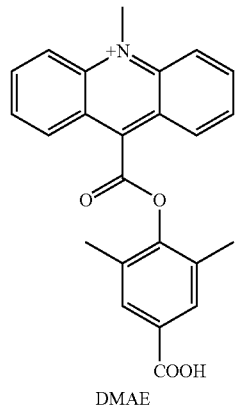

DMAE

TABLE 1

Chemiluminescence from Acridinium Compounds

| Compound | % Signal Retained | Chemiluminescence Triggering Reagent |
|---|---|---|
| DMAE | 0.14 | 1% $H_2O_2$ + 0.5% CTAC in 0.2 M sodium carbonate, pH 9 |
| 2,7-dimethoxy-DMAE | 9.5 | 1% $H_2O_2$ + 0.5% CTAC in 0.2 M sodium carbonate, pH 9 |
| 2-CME-7-methoxy-DMAE | 43 | 1% $H_2O_2$ + 0.5% CTAC in 0.2 M sodium carbonate, pH 8.3 |
| NSP-AS | 6.3 | 1% $H_2O_2$ + 0.5% CTAC in 0.2 M sodium carbonate, pH 8.3 |
| NSP-AS | 13.4 | 1% $H_2O_2$ + 0.5% CTAC in 0.2 M sodium carbonate, pH 9 |
| 2-hydroxy-DMAE | 5.8 | 1% $H_2O_2$ + 0.5% CTAC in 0.2 M sodium carbonate, pH 9 |
| DMAE-anti-TSH | 0.18 | 1% $H_2O_2$ + 0.5% CTAC in 0.2 M sodium carbonate, pH 9 |
| 2,7-dimethoxy-DMAE-anti-TSH | 60 | 1% $H_2O_2$ + 0.5% CTAC in 0.2 M sodium carbonate, pH 9 |

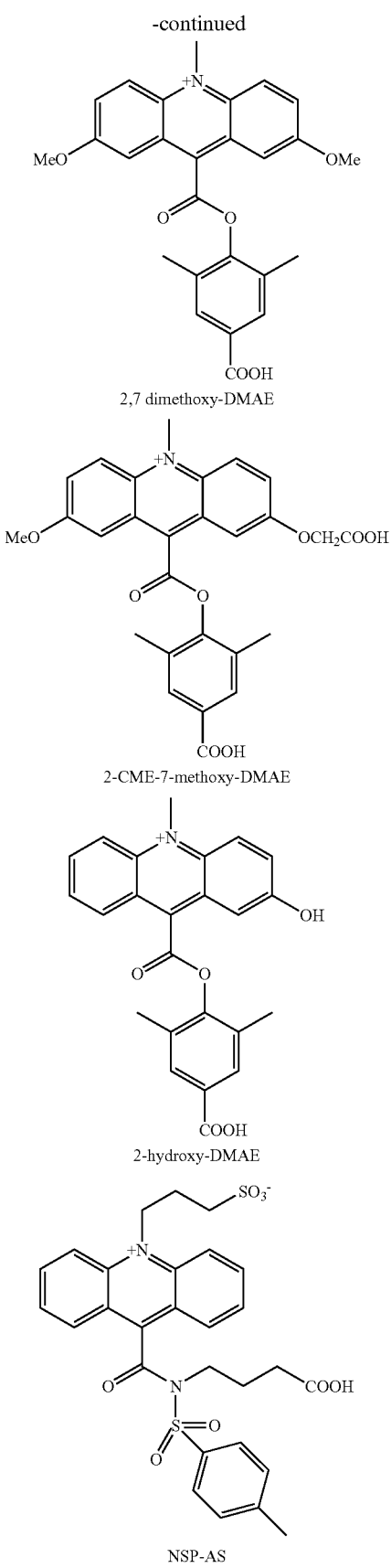

2,7 dimethoxy-DMAE

2-CME-7-methoxy-DMAE 2-hydroxy-DMAE

NSP-AS

Thus, 2-hydroxy-DMAE and 2,7-dimethoxy-DMAE are each acridinium esters with electron-donating groups. The hydroxy group in 2-hydroxy-DMAE is the electron-donating group whereas the two methoxy groups in 2,7-dimethoxy-DMAE are electron-donating groups. In addition, even in the absence of an electron-rich acridinium nucleus, chemiluminescence from the acridinium sulfonamide can be triggered at mild pH. It is not known why this is possible for the acridinium sulfonamide (NSP-AS) even in the absence of electron-donating groups.

Homogeneous Assays Using Signal Modulation of Antibody-Bound Tracer (a) Acridinium Esters The acridinium ester, 2,7-dimethoxy-DMAE was conjugated to three analytes: valproate, theophylline and carbamazepine to form tracers that are commonly measured by immunochemical techniques. The process steps for making conjugates of acridinium compounds to various other molecules of interest are well known to those skilled in the art of organic synthesis. A conjugate of an acridinium compound is comprised of the acridinium compound and the molecule of interest with a covalent bond linking the two moieties. The molecule of interest can be a small molecule such as a steroid, a therapeutic drug, a vitamin, a hormone and small peptides, or a macromolecule such as a protein, nucleic acid, oligosaccharide, antibody, antibody fragment, cell, virus and synthetic polymer. Examples of proteins include avidin, strepavidin, neutravidin, receptors, and allergens.

The covalent bond can be an amide bond, an ester bond, an ether bond, a bond linking two carbon atoms, and the like. Formation of the covalent bond between the acridinium compound and the molecule of interest is generally accomplished by a chemical reaction between complementary reactive functional groups on the two moieties. For example, an amide bond is made from a carboxylic acid functional group on one molecule and an amino group on the second molecule. Typically, the process involves converting the carboxylic acid to a reactive form such as an active ester or an anhydride followed by reaction with the amino group.

It was initially envisioned to label the antibodies corresponding to these analytes with fluors and perform homogeneous assays using resonance energy transfer from the acridinium tracer to the fluor on the antibody. However, experimentation revealed that antibody binding to the corresponding tracer for all three analytes resulted in an unexpected enhancement in light production for the acridinium ester when measured over at period of a few seconds. Therefore, it was not necessary to label the antibodies corresponding to these analytes with fluors.

The magnitude of the light enhancement for the acridinium ester was different for the three analytes. This can reflect differences in the affinities and/or microenvironment of these three different antibodies for their respective haptens.

Faster kinetics of light emission from the acridinium ester antibody-bound tracer as compared to the free tracer is one possible mechanism for the observed increase in chemiluminescent signal. Enhancement of chemiluminescence of an isoluminol-biotin conjugate upon binding to avidin has been reported by Schroeder et al, *Anal. Chem.* vol. 48, pages 1933-1937 (1976).

For all three analytes, valproate, theophylline and carbamazepine, the chemiluminescent signal from the binding reactions could be measured directly without dilution. These small molecule assays are thus extremely simple to perform. The steps involved in devising and carrying out a homogeneous assay for the measurement of a small molecule analyte include forming a conjugate of the small molecule analyte and the acridinium compound as already described and making a solution of the conjugate in an appropriate solvent, such as a mixture of an organic solvent, for example, dimethyl formamide and water or a buffer. The acridinium compound is either an acridinium ester with electron-donating functional groups at the C2 and/or C7 position or an acridinium sulfonamide with or without electron-donating functional groups at the C2 and/or C7 position.

The conjugate is used to screen various antibodies of the analyte to select an antibody which upon binding to the acridinium conjugate causes an alteration in the intensity of light emission from the acridinium conjugate when its chemiluminescence is triggered at a pH of about 6-10.

The conjugate is used to generate a dose-response cure using a series of 'standards' which comprise different known concentrations of the analyte in a fluid, typically serum. Generally this is accomplished by mixing a fixed concentration of the acridinium conjugate to each standard in a fixed volume of buffer and adding a limited quantity of the desired antibody which is capable of forming a complex with either the analyte or its acridinium conjugate in solution.

The solution containing the analyte, the conjugate and the antibody is then incubated for a fixed length of time, typically about 10 to 60 minutes at room temperature, to form a reaction mixture.

The chemiluminescence of the reaction mixture is then or triggered at a pH of about 6 to 10 by adding chemiluminescence triggering reagents such as a solution of hydrogen peroxide in a buffer such as carbonate, borate, phosphate, and tris. The chemiluminescence is then measured with a luminometer. A dose response curve is then prepared by plotting the observed chemiluminescence versus the concentration of the analyte in the standard.

The concentration of an unknown sample of the analyte is then determined by incubating the sample at the same conditions as the standard solution. The chemiluminescence of the unknown sample of analyte is then triggered with the same triggering agent used to trigger the chemiluminescence of the standard analyte and its concentration is determined from the dose response curve.

Homogeneous assays for carbamazepine, theophylline and valporate were performed using the 2,7-dimethoxy-DMAE tracers in a small volume (0.2 mL) of buffer. The tracer at nanomolar concentrations was mixed with the hapten standards in human serum. The binding reactions were initiated by the addition of a limited quantity of the corresponding antibody. These are true competitive assays because the analyte and the tracer compete for a limited amount of antibody.

As the concentration of the hapten increased, the concentration of antibody-bound tracer decreased and consequently, the chemiluminescent signal for the acridinium ester was depressed proportionally.

(b) Acridinium Sulfonamides

Chemiluminescent triggering under mild conditions of hapten conjugates of acridinium sulfonamides showed characteristics that contrasted sharply to what was observed with acridinium esters. For acridinium esters, tracer binding to the antibody leads to an increase in chemiluminescence whereas for acridinium sulfonamides, tracer binding by the antibody leads to a decrease in chemiluminescence. Slower kinetics of light emission from the acridinium sulfonamide antibody-bound tracer is a possible mechanism for the observed decrease in chemiluminescent signal. The relative luminescent yield of the acridinium sulfonamide derived tracer was dependent upon the conjugated hapten. In addition, electron donating functional groups are not needed at the C2 and/or C7 positions to trigger chemiluminescence.

In comparison to the free tracers, antibody-bound tracers exhibited a decrease in luminescence when their chemiluminescence was measured for a few seconds. The antibody bound valproate, theophylline and carbamazepine tracers exhibited 28%, 12% and 5% of the relative luminescence of the free tracers. A kinetic profile of the light production revealed a decrease in the chemiluminescent reaction rate upon antibody binding. This phenomenon was used to devise homogeneous assays for the analytes: valproate, theophylline and carbamazepine.

Homogeneous Assays Using Quenching

In addition to signal modulation due to tracer binding by an antibody, an alternate construct for a homogeneous assay using the acridinium compounds of this invention entails using the phenomenon of signal quenching as a mechanism to generate a dose response curve.

Signal quenching reduces the chemiluminescence of the acridinium compound by using an acceptor molecule which absorbs energy from the acridinium compound but does not have an emission of its own. The acridone is the chemical species that is formed in an electronically-excited state from the chemical reaction of the acridinium compound with hydrogen peroxide. Any molecule that can absorb the electronic excitation energy of the acridone, which normally is emitted as light, and dissipate it via non-radiative pathways can perform this quenching function. Dabsyl is commonly used for this purpose.

In the antibody-tracer complex, the spatial proximity of the antibody and the acridinium compound-derived tracer suggests that excited-state energy from the acridinium compound may be transferred to suitable acceptor molecules on the antibody. To investigate this matter further, a valproate tracer of 2-CME-7-methoxy-DMAE was prepared. See Example 2.

This tracer when incubated with an unlabeled valproate antibody did not shout any modulation of its chemiluminescent signal. When the antibody was labeled with the quencher dabsyl, antibody-bound tracer showed a drop in luminescence. Thus, tracer binding to the dabsyl-labeled antibody could be measured by recording a concomitant decrease in chemiluminescent signal.

In an assay that uses the principle of signal-quenching, all steps are the same as the homogeneous assay using signal modulation except that the conjugate of an antibody and a quencher is used.

A valproate assay was devised using the quenching phenomenon. The valproate antibody used previously with the 2,7-dimethoxy-DMAE-valproate conjugate was labeled with the synthetic dabsyl derivative dabsyl-ED-glutarate-NHS ester. The dabsyl derivative was synthesized by first condensing dabsyl chloride with ethylene diamine followed by reaction with glutaric anhydride and subsequent conversion of the resulting carboxylic acid to the N-hydroxy succinimide (NHS) ester.

A homogeneous assay using the labeled antibody was performed by allowing the tracer and the valproate standard in sheep serum to compete for a limited amount of the dabsyl-labeled antibody. An increase in the concentration of valproate led to an increase in chemiluminescent signal.

Homogeneous Assays Using Chemiluminescence Resonance Energy Transfer

The chemiluminescent Resonance Energy Transfer (RET) immunoassay is based on formation of a complex consisting of the analyte with two binding partners, for example antibodies. Fabs, lectins enzymes and nucleic acid binding ligands can also be employed in an analogous fashion, where one is labeled with the chemiluminescent donor compound and the second, directed against another epitope on the analyte, is labeled with a fluorophore acceptor. Upon binding, the analyte becomes the bridge between the donor and the acceptor permitting efficient RET if the two are within less than 10 nm distance. Triggering the chemiluminescence with the light releasing reagents produces light that is transferred to the acceptor and measured at its optimum wavelength.

In principle, the analytes measured in the chemiluminescent Resonance Energy Transfer immunoassay are macromolecules having at least two binding sites in the same molecule. Such macromolecules include the group consisting of proteins, nucleic acids, oligosaccharides, antibodies, antibody fragments, cells, viruses, and synthetic polymers.

The process steps for a chemiluminescent homogeneous resonance energy transfer assay for the measurement of a macromolecular analyte such as a protein include making a first conjugate of an antibody to the analyte using the acridinium compounds of the present invention wherein covalent bond formation is carried out between the antibody and functional groups located on the acridinium nucleus of the acridinium compound. The acridinium compound is either an acridinium ester with electron-donating groups at the C2 and/or C7 position, or an acridinium sulfonamide with or without electron-donating groups at the C2 and/or C7 position.

A second conjugate of a second antibody to the analyte is made using an "acceptor" molecule which can absorb electronic excitation energy from the first acridinium-antibody conjugate. This second antibody must bind to a different region of the analyte but must also bind sufficiently close to the first antibody so that energy transfer from the acridinium compound and the acceptor can occur. The distance between regions is generally $\leq$10 nm. The acceptor molecule can either re-emit the absorbed energy from the acridinium compound at a different wavelength of light or dissipate it as heat.

The first and second conjugates are used to generate a dose-response curve using a series of 'standards' which comprise different known concentrations of the analyte in a fluid, typically serum. This is generally accomplished by mixing fixed concentrations of the acridinium conjugates to each standard in a fixed volume of buffer. The solution containing the analyte, and the two conjugates is called the "reaction mixture" and is incubated for about 10 to 60 minutes at ambient or room temperature.

The chemiluminescence of the reaction mixture is triggered in the pH range of about 6 to 10 by adding chemiluminescence triggering reagents such as a solution of hydrogen peroxide in a buffer and measuring the chemiluminescence using a luminometer. The luminometer must be capable of distinguishing chemiluminescent signals emitted at two different wavelengths. A dose response curve is then prepared by plotting the observed chemiluminescence versus the concentration of the analyte in the standard.

The concentration of an unknown sample of the analyte is determined by incubating the reaction mixture of the unknown analyte at the same conditions as the standard analyte reaction mixture. The chemiluminescence of the unknown reaction mixture is then triggered using the same triggering agent and the same conditions used to prepare the standard dose response curve. The concentration of the unknown sample is then determined from the dose response curve.

In the resonance energy transfer assay for the analyte HCG described in Example 13, one antibody is conjugated with an acridinium ester while the second antibody is conjugated with the fluorescent compound naphthofluorescein.

Labeled Biotins

Avidin Complex

A homogeneous resonance energy transfer assay for the measurement of the vitamin biotin can be performed by making a conjugate of biotin to the acridinium compounds of the present invention wherein covalent bond formation is carried out between biotin and functional groups located on the acridinium nucleus of the acridinium compound. The acridinium compound is either an acridinium ester with electron-donating groups at the C2 and/or C7 position or an acridinium sulfonamide with or without electron-donating groups at the C2 and/or C7 position.

A second conjugate of biotin is made using a molecule called an "acceptor" which can absorb electronic excitation energy from the acridinium compound-biotin conjugate. The acceptor molecule can either re-emit the absorbed energy at a different wavelength of light or dissipate it as heat.

The above conjugates are used to generate a dose-response curve for biotin using a series of biotin standards which comprise different known concentrations of biotin in a fluid, typically serum. Generally this is accomplished by mixing fixed concentrations of the two biotin conjugates and neutravidin or streptavidin to each biotin standard in a fixed volume of buffer. The solution containing biotin, the two conjugates and the neutravidin or streptavidin, termed the "reaction mixture" is incubated for about 10 to 60 minutes at ambient temperature.

The chemiluminescence of the reaction mixture is triggered in the pH range of about 6 to 10 by adding chemiluminescence triggering reagents such as a solution of hydrogen peroxide in buffer and measuring the chemiluminescence using a luminometer. The luminometer must be capable of distinguishing chemiluminescent signals emitted at two different wavelengths. A dose response curve for biotin is prepared by plotting the observed chemiluminescence versus the concentration of biotin in the standard.

The concentration of an unknown sample of biotin is measured by first incubating the reaction mixture of the unknown sample at the same conditions used for the standard reaction mixture. The chemiluminescence of the unknown sample of biotin is then triggered with the same triggering agents and at the same conditions as the known reaction mixture. The concentration of the unknown sample of biotin is determined from the concentration on the dose response curve corresponding to the measured chemiluminescence.

A convenient model to test the limits of RET with the acridinium compounds of the present invention serving as the donor, and a fluorescent acceptor was to attach them to a biotin, a low molecular weight molecule, to form a conjugate. This then allows the resulting conjugates to bind to avidin, a protein with multiple binding sites for biotin. Because the dimensions of avidins are about 30×40×50 A°, the bound labeled biotin species would be in close proximity thereby permitting RET. Hence, biotin-hexaethyleneglycol-2-CME-7-methoxy-DMAE (biotin-AE) and biotin-jeffamine-napthofluorescein (biotin-NPFL) were synthesized. CME is carboxymethylether. See Example 10. Example 11 details the resonance energy transfer assay for the measurement of biotin. In the resonance energy transfer assay for biotin described in Example 12, biotin conjugates of the acridinium ester, 2-CME-7-methoxy-DMAE and the fluorescent compound naphthofluorescein are used in conjunction with neutravidin.

Sandwich Assay for HCG

This is a homogeneous assay for HCG using the principle of resonance energy transfer. In this assay, an anti-HCG antibody labeled with the novel acridinium compounds of the present invention, and a second anti-HCG antibody, directed against another site, labeled with a fluorophore form a complex with HCG, a large molecular weight analyte. Several anti-HCG antibodies were labeled to varying extent with 2-CME-7-methoxy-DMAE or naphthofluorescein. An anti-HCG-wholo and an anti-HCG-beta pair were bound sufficiently close to each other to produce RET. As chemiluminescence (480 nm) was triggered, the emission shifted to the fluorophore maximum measured at >650 nm. A maximum of ~3-fold increase in signal over background was observed at 5000 mIU/mL HCG. The data appear in Table 2.

TABLE 2

Homogeneous CL RET For HCG

| HCG mIU/mL | NET RLU |
|---|---|
| 0 | 89,445 |
| 100 | 92,920 |
| 500 | 114,530 |
| 1,000 | 130,325 |
| 2,500 | 183,180 |
| 5,000 | 242,860 |
| 7,500 | 243,025 |
| 10,000 | 232,905 |
| 20,000 | 199,640 |

In summary, the chemiluminescence of certain acridinium compounds can be triggered at mild pH. Hapten tracers derived from these acridinium compounds when complexed to their respective antibodies show either an enhancement (acridinium esters) or attenuation (acridinium sulfonamides) of light emission. This novel discovery enabled the development of simple homogeneous assays for such clinically important analytes as theophylline, valproate and carbamazepine. In addition, the acridinium compounds described herein can be used in resonance energy transfer assays.

Example 1

This example describes the syntheses of the electron rich acridinium ester, 2,7-dimethoxy-DMAE and its hapten conjugates. Therein, 2,7-dimethoxy acridine-9-carboxylic acid was synthesized using the procedure described in Zomer at al., "Synthesis, Chemiluminescence, and Stability of Acridinium Ester Labeled Compounds", *Pract. Spectroc.* (Lumin. Tech. Biochem. Anal.), vol. 12, pages 505-511 (1991), and condensed with 4-carboxybenzyl-2,6-dimethylphenol. The resulting acridine ester was N-methylated with methyl triflate. Removal of the benzyl ester protecting group exposed the carboxylic acid. The subsequent formation of the valproate, carbamazepine and theophylline conjugates was accomplished via the active NHS ester.

(a) Synthesis of 2,7-dimethoxy-2',6'-dimethyl-4'-benzyloxycarbonylphenyl acridine-9-carboxylate 2,7-Dimethoxyacridine-9-carboxylic acid (0.5 g, 0.177 mmol) in anhydrous pyridine (25 mL) was cooled in an ice bath under a nitrogen atmosphere and treated with p-toluenesulfonyl chloride (0.674 g, 2 equivalents) and after 10 minutes, 4-carboxybenzyl-2,6-dimethylphenol (0.453 g, 1 equivalent) was added. The reaction was warmed to room temperature. After 1-2 hours, am additional 2 equivalents p-toluenesulfonyl chloride was added along with 0.5 equivalent phenol and pyridine (10-15 mL). The reaction was stirred at room temperature under a nitrogen atmosphere for 48 hours. The solvent was then removed under reduced pressure and the residue was dissolved in chloroform (50 mL). This solution was washed with 2% aqueous sodium bicarbonate followed by 2% aqueous ammonium chloride. The chloroform extract was then dried over magnesium sulfate and evaporated to dryness. The product was purified by TLC on silica using 5% ethyl acetate, 95% chloroform. Rf=0.5. Yield=0.663 g (72%)

(b) Synthesis of 2,7-dimethoxy-2',6'-dimethyl-4'-benzyloxycarbonylphenyl-10-methylacridinium-9-carboxylate The acridine ester from (a) above (0.15 g, 0.29 mmol) in dichloromethane (5 ml) was treated with solid sodium bicarbonate (60 mg, 0.71 mmol) and methyl trifluoromethane sulfonate (0.2 mL, 0.82 mmol). The reaction was stirred at room temperature for 16 hours and then methanol (5 mL) was added and the reaction was filtered through glass wool. HPLC analysis of the filtrate on a C18 4.6 mm×30 cm column and using a 30-minute gradient of 10%->100% MeCN/water each containing 0.05% trifluoroacetic acid at a flow rate of 1 mL/min and UV detection at 260 nm, indicated >90% conversion to product eluting at 21 minutes. The filtrate was evaporated to dryness and the crude product was used as such for the next reaction.

(c) Synthesis of 2,7-dimethoxy-2',6'-dimethyl-4'-carboxyphenyl-10-methylacridinium-9-carboxylate (2,7-dimethoxy-DMAE)

The acridinium ester from (b) above (25 mg) was treated with 30% HBr/AcOH (3 mL) and the reaction was stirred at room temperature for 4 hours. The product was precipitated by the addition of ether (~50 mL). The ether was decanted and the residue was rinsed several times with ether and dried by rotary evaporation. Yield=16 mg. HPLC analysis using the gradient described above showed product eluting at 15 minutes.

(d) Synthesis of 2,7-dimethoxy-2',6'-dimethyl-4'-[N-succinimidyl]oxycarbonyl-phenyl 10-methylacridinium-9-carboxylate (2,7-dimethoxy-DMAE-NHS)

The acridinium carboxylic acid from (c) above (16 mg, 0.03 mmol, bromide counter ion) was dissolved in 25% anhydrous MeCN, 75% anhydrous dimethylformamide (DMF) (4 mL) and treated with N-hydroxysuccinimide (17 mg, 5 equivalents) and dicyclohexyl carbodiimide (DCC) (31 mg, 5 equivalents). The reaction was stirred at room temperature under a nitrogen atmosphere for 16 hours. HPLC analysis using the gradient described above indicated complete conversion with the product eluting at ~16 minutes. The product was purified by preparative HPLC using a 20 mm×30 cm column. The HPLC fractions containing the product were lyophilized to dryness to afford a bright yellow powder. Yield=12.6 mg.

(e) Synthesis of 2,7-dimethoxy-DMAE-valproate 2,7-Dimethoxy-DMAE-NHS (1 mg, 1.84 umoles) in DMF (0.1 mL) was cooled in an ice bath and treated with 6-amino-2-propyl-hexanoic acid [0.64 mg, 2 equivalents, Sidki et al, *J.*

*Clin. Chem. Biochem.* vol. 26 (2), page 69, (1988)] dissolved in 100 mM sodium carbonate pH 9 (0.1 mL). The reaction was stirred at room temperature. After 1 hour, HPLC analysis using the gradient described above, indicated complete disappearance of starting material and the formation of a product eluting a few minutes later. This product was purified by preparative HPLC using a 7.8 mm×30 cm column. The HPLC fractions containing product were lyophilized to dryness to afford a yellow powder. Yield=~1 mg; MALDI-TOF MS 603.1 obs. (601.7 calc.).

(f) Synthesis of 2,7-dimethoxy-DMAE-HD 2,7-Dimethoxy-DMAE (7 mg, 13.3 umoles) was dissolved in a mixture of anhydrous MeCN/DMF (2 mL, 1:3) and treated with N hydroxysuccinimide (9 mg, 5 equivalents) and DCC (16 mg, 5 equivalents). The reaction was stirred at room temperature after 3 hours, 5 equivalents each of N-hydroxysuccinimide and DCC were added. The resulting reaction was stirred at room temperature for 16 hours. The reaction mixture was then filtered through glass wool and treated with 1,6-hexanediamine (HD, 18.3 mg, 10 equivalents) dissolved in 100 mM sodium carbonate pH 9 (2 mL). The reaction was stirred at room temperature. After 2 hours, HPLC analysis using a 4.6×30 cm C18 column and a 40-minute gradient of 10%->60% MeCN/water (each with 0.05% TFA) at a flow rate of 1 mL/min and UV detection at 260 nm indicated product eluting at ~23 minutes. This was purified by preparative HPLC using a 20 mm×30 cm column. The HPLC fractions containing product were lyophilized to dryness.

Yield=9.6 mg (94%); MALDI-TOF MS 545.8 obs. (544.7 calc.).

(g) Synthesis of 2,7-dimethoxy-DMAE-HD-theophylline

8-Carboxypropyltheophylline (5 mg, 18.8 umoles, Sigma) was dissolved in anhydrous DMF (1 mL) and treated with N-hydroxysuccinimide (11 mg, 5 equivalents) and DCC (20 mg, 5 equivalents). The reaction was stirred at room temperature for 16 hours. 2,7-Dimethoxy-DMAE-HD (3.3 mg, 4.3 umoles) was then added as a solution in methanol (0.2 mL) followed by N,N-diisopropylethylamine (3.2 uL, 18.4 umoles). After three hours HPLC analysis using the 10%->60% gradient described above indicated product eluting at ~28 minutes. This product was isolated by preparative HPLC using a 20 mm×30 cm column. The HPLC fractions containing product were lyophilized to dryness. Yield=2.7 mg (76%); MALDI-TOF MS 794.2 obs. (792.9 calc.).

(h) Synthesis of 2,7-dimethoxy-DMAE-HD-SA-ED-Carbamazepine

Carbamazepine-ED-SA was prepared in two steps from carbamazepine-N-acid chloride that was provided by the Central Research Labs of Ciba-Geigy Limited, now-Novartis Inc. A solution of carbamazepine-N-acid chloride (2 g, 7.828 mmol) in 10 ml of tetrahydro furan was dropwise added to a solution of ethylene diamine (5.24 ml, 10 equivalents) in 100 ml of ether at 0° C. The reaction was allowed to stir at room temperature for 1.5 hr, and then was evaporated under reduced pressure with the help of xylene. The solid obtained was transferred to a fritted funnel and washed with chloroform three times to give carbamazepine-ED as an off-white material in 955 mg. The carbamazepine-ED (950 mg, 3.42 mmol) was suspended in a mixed solvent of 70 ml of DMF/chloroform (1:1), followed by addition of succinic anhydride (513 mg, 1.5 equivalents) and triethylamine (1.9 ml, 4 equivalents). The mixture was heated with stirring at 100° C. for an hour to give a homogeneous solution. It was evaporated under reduced pressure to dryness. The residue was treated with 60 ml of water. The suspension was stirred at room temperature 50 minutes to form a white precipitate. It was collected and washed with water and then chloroform.

After it dried under vacuum, 552 mg of carbamazepine-ED-SA was obtained. Carbamazepine-ED-SA (5 mg, 13.2 umoles) in anhydrous DMF (0.5 mL) was treated with N-hydroxysuccinimide (7.6 mg, 5 equivalents) and DCC (13.6 mg, 5 equivalents). The reaction was stirred at room temperature for 3-4 hours and then 1.7 mg of the active ester was withdrawn and diluted to 900 uL DMF. This solution was treated with a solution of 2,7-dimethoxy-DMAE-HD (2.5 mg, 3.24 umoles) in methanol (0.2 mL) along with N,N-diisopropylethylamine (2.4 uL, 13.8 umoles). The reaction was stirred at room temperature for 16 hours. HPLC analysis using the 10%->60% gradient described above indicated product eluting at ~34 minutes. The product was purified by preparative HPLC using a 20 mm×30 cm column and the HPLC fractions containing product were lyophilized to dryness. Yield=1.6 mg (54%); MALDI-TOF MS 907.8 obs. (906.1 calc.).

(i) Synthesis of 2,7-dimethoxy-DMAE-Anti-TSH Conjugate

Anti-TSH monoclonal antibody (0.5 mg, 3.33 nmoles) in a mixture of 100 mM sodium phosphate pH 8 (0.1 mL) and PBS pH 8 (80 uL) was treated with a solution of 2,7-dimethoxy-DMAE-NHS (36.2 ug, 20 equivalents) in DMF (20 uL). The reaction was stirred at 2-4° C. in a cold-box for 16 hours and then the labeled protein was isolated by Sephadex G25 gel-filtration chromatography using water as eluent. The conjugate eluting in the void volume of the column was collected and concentrated to ~1 mL. This solution was diluted with 4 mL PBS pH 7.4 also containing 1% BSA and 0.05% sodium azide and stored at 4° C. The following reaction equations represent the synthesis of 2,7-dimethoxy-DMAE and conjugates.

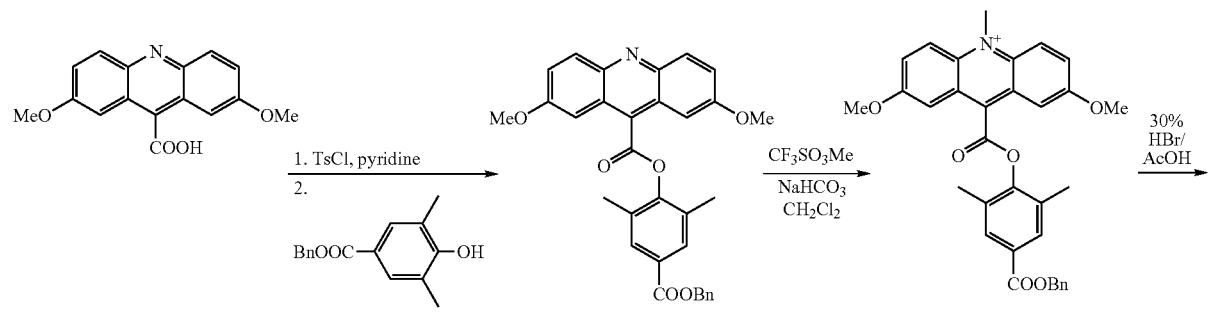

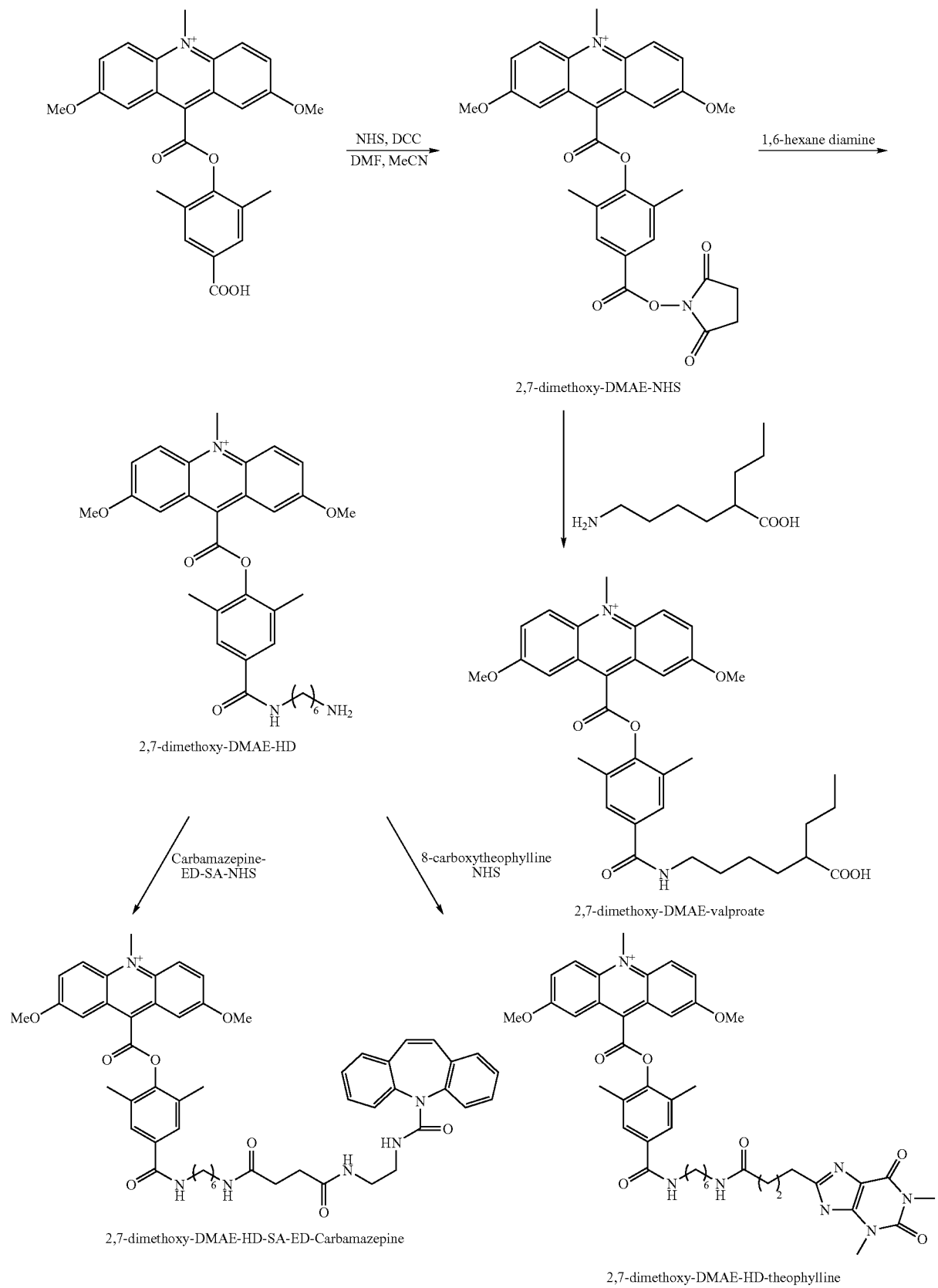

Example 2

(a) Synthesis of 2-CME-7-methoxy-DMAE

The synthesis of 2-CME-7-methoxy-DMAE was accomplished from 5-methoxyisatin and 4-bromophenol. N-Alkylation of the sodium salt of 5-methoxyisatin with 4-benzyloxybromobenzene followed by rearrangement in hot alkali afforded the functionalized acridine carboxylic acid which was condensed with 4-nitro-2,6-dimethyl phenol. The benzyl ether in the resulting acridine ester was first cleaved off and the free hydroxyl group was alkylated with benzyl bromoacetate. Methylation of the acridine nitrogen with methyl triflate followed by conversion of the benzyl ester to the free acid completed the synthesis. The acridinium compound was converted to the valproate conjugate via the NHS ester.

(b) Synthesis of 4-benzyloxybromobenzene

4-Bromophenol (2 g, 0.0116 mol) in acetone (40 mL) was treated with potassium carbonate anhydrous (1.91 g, 1.2 equivalents) and benzyl bromide (1.44 mL, 1.05 equivalents). The reaction was refluxed under a nitrogen atmosphere. After 5-6 hours reflux, the reaction was cooled to room temperature and diluted with an equal volume of ethyl acetate. This solution was washed with water, dried over anhydrous magnesium sulfate and evaporated to dryness. A white fluffy solid was obtained. Yield=2.36 g (73%).

(c) Synthesis of N-[4'-benzyloxy)phenyl]-5-methoxyisatin

5-Methoxyisatin (1.5 g, 0.85 mmol) in anhydrous DMF (50 mL) was cooled in an ice bath under a nitrogen atmosphere and treated with sodium hydride (0.25 g, 1.2 equivalents). The reaction was stirred in the ice bath and after 15-20 minutes, 4-benzyloxybromobenzene (2.36 g, 0.85 mmol) was added as a solution in anhydrous DMF (3 mL) along with copper iodide (3.23 g, 2 equivalents). The reaction was heated in an oil bath under a nitrogen atmosphere at 130° C. for 24 hours. The reaction was then cooled to room temperature and filtered and the filtrate was evaporated to dryness. The crude material was purified by flash chromatography on silica gel using 35% ethyl acetate in hexanes as eluent. The N-alkylated isatin derivative was isolated as an orange-brown solid. Yield 1 g (32%).

(d) Synthesis of 2-benzyloxy-7-methoxy acridine-9-carboxylic acid

The N-alkylated isatin from (b) above (1 g) was suspended in 10% potassium hydroxide (100 mL) and refluxed under a nitrogen atmosphere. After 4 hours, the reaction was cooled for 5-10 minutes and then filtered while still hot. A yellow precipitate separated in the filtrate. The filtrate was diluted with ice and water and was then acidified with a mixture of concentrated HCl and ice until a thick yellow precipitate separated out. This was allowed to stand for ~15 minutes and was then filtered using a medium porosity fritted glass funnel. The product was subsequently rinsed with dry ether and then air dried. The resulting yellow powder was then transferred to a round bottom flask, suspended in anhydrous toluene and evaporated to dryness. Yield=0.75 g (75%).

(e) Synthesis of 2-benzyloxy-7-methoxy-2',6'-dimethyl-4'-nitrophenyl acridine-9-carboxylate 2-Benzyloxy-7-methoxy acridine-9-carboxylic acid (0.38 g, 0.106 mol) from (c) above in anhydrous pyridine (30-40 mL) was treated with p-toluenesulfonyl chloride (0.404 g, 2 equivalents) at 0° C. under nitrogen. After 5 minutes, 2,6-dimethyl-4-nitrophenol (0.177 g, 1 equivalent) was added and the reaction was warmed to room temperature and stirred for 24 hours. The solvent was then removed under reduced pressure and the residue was dissolved in chloroform (50 mL). This solution was wished with 3% aqueous sodium bicarbonate and then 3% aqueous ammonium chloride. The chloroform extract was then dried over anhydrous magnesium sulfate and evaporated to dryness. The crude product was purified by preparative TLC on silica using 70% hexanes, 25% chloroform, 5% ethyl acetate. Yield=0.26 g (48%)

(f) Synthesis of 2-hydroxy-7-methoxy-2',6'-dimethyl-4'-nitrophenyl acridine-9-carboxylate The 2-benzyloxy-7-methoxy acridine ester from (d) above (0.2 g) was stirred in a mixture of 30% HBr/AcOH (10 mL) and dimethyl sulfide (5 mL) at room temperature for 4 hours. The product was then precipitated by the addition of anhydrous ether followed by filtration. A bright yellow solid was obtained. HPLC analysis using a 4.6 mm×30 cm C18 column and a 30-minute gradient of 10%->70% MeCN/water (each containing 0.05% TFA) at a flow rate of 1 mL/min and UV detection at 260 nm, indicated product eluting at ~25 minutes (starting material elutes at 34 minutes). Yield=0.24 g.

(g) Synthesis of 2-[benzyloxycarbonyl]methyloxy-7-methoxy-2',6'-dimethyl-4'-nitrophenyl acridine-9-carboxylate The compound from (e) above (0.163 g, 0.38 mmol) in anhydrous DMF (10 mL) was treated with potassium carbonate anhydrous (65 mg, 1.2 equivalents) followed by benzyl bromoacetate (66.2 uL, 1.1 equivalents). The reaction was heated in an oil bath at 65° C. under a nitrogen atmosphere. After one hour, HPLC analysis using the gradient described above indicated >85% conversion with the product eluting at 32 minutes. The reaction was then cooled to room temperature and the solvent was removed under reduced pressure. The residue was dissolved in chloroform (50 mL) and this solution was washed once with 3% aqueous ammonium chloride and 3% aqueous sodium bicarbonate. The chloroform extract was then dried over anhydrous magnesium sulfate and evaporated to dryness. The crude product (0.3 g) was used as such for the next reaction.

(h) Synthesis of 2-[benzyloxycarbonyl]methyloxy-7-methoxy-2',6'-dimethyl-4'-nitrophenyl-10-methyl acridinium-9-carboxylate The crude acridine ester from (f) above (0.3 g, 0.53 mmol) was dissolved in dichloromethane (~5 mL) and treated with sodium bicarbonate (0.44 g, 10 equivalents) and methyl trifluoromethane sulfonate (0.6 mL, 10 equivalents). The reaction was stirred at room temperature for 16 hours. HPLC analysis using the gradient described above showed complete conversion with the product eluting at 25 minutes. The reaction was filtered through glass wool and the filtrate was evaporated to dryness. A bright yellow solid was recovered that was used directly for the next reaction. MALDI-TOF MS 582.4 obs. (581.6 calc.).

(i) Synthesis of 2-carboxymethylether-7-methoxy-2', 6'-dimethyl-4'-nitrophenyl-methyl acridinium-9-carboxylate (2-CME-7-methoxy-DMAE)

The crude acridinium ester from (g) above was stirred in 30% HBr/AcOH (10 mL) at room temperature for 4-5 hours. Anhydrous ether was then added to precipitate the product which was collected by filtration. This precipitate was rinsed several times with ether and then air dried. A reddish-yellow powder was obtained. HPLC analysis using the gradient described earlier indicated clean conversion to product eluting at 20 minutes. Yield=0.128 g; MALDI-TOF MS 492.2 obs. (491.5 calc.).

(j) Synthesis of 2-CME-7-methoxy-DMAE NHS ester

2-CME-7-methoxy-DMAE (10 mg, 16.6 umoles) in MeCN (2 mL) was treated with N-hydroxysuccinimide (2.9 mg, 1.5 equivalents) and DCC (17 mg, 5 equivalents). The reaction was stirred at room temperature for 1-2 hours by which time a fine precipitate of DCU had formed in the reaction. The reaction was filtered through glass wool and the solution was evaporated to dryness. MALDI-TOF MS 589.1 obs. (588.6 calc.).

(k) Synthesis of 2-CME-7-methoxy-DMAE-Valproate Conjugate

An ice-cold solution of 6-amino-2-propylhexanoic acid (13 mg, 75 μmol) in sodium phosphate buffer (0.10 M, pH 7.4, 0.70 ml) was mixed with an ice-chilled solution of 2-CME-7-methoxy-DMAE NHS ester (1.0 mg, 1.7 μmol) in DMF (0.30 ml). This mixture was allowed to stir at room temperature overnight. The desired product was isolated from C-18 reversed phase HPLC and lyophilized. MALDI-TOF MS 646.1 obsd. (645.7 calcd). The following reaction equations represent the synthesis of 2-CME-7-OMe-DMAE and valproate conjugate.

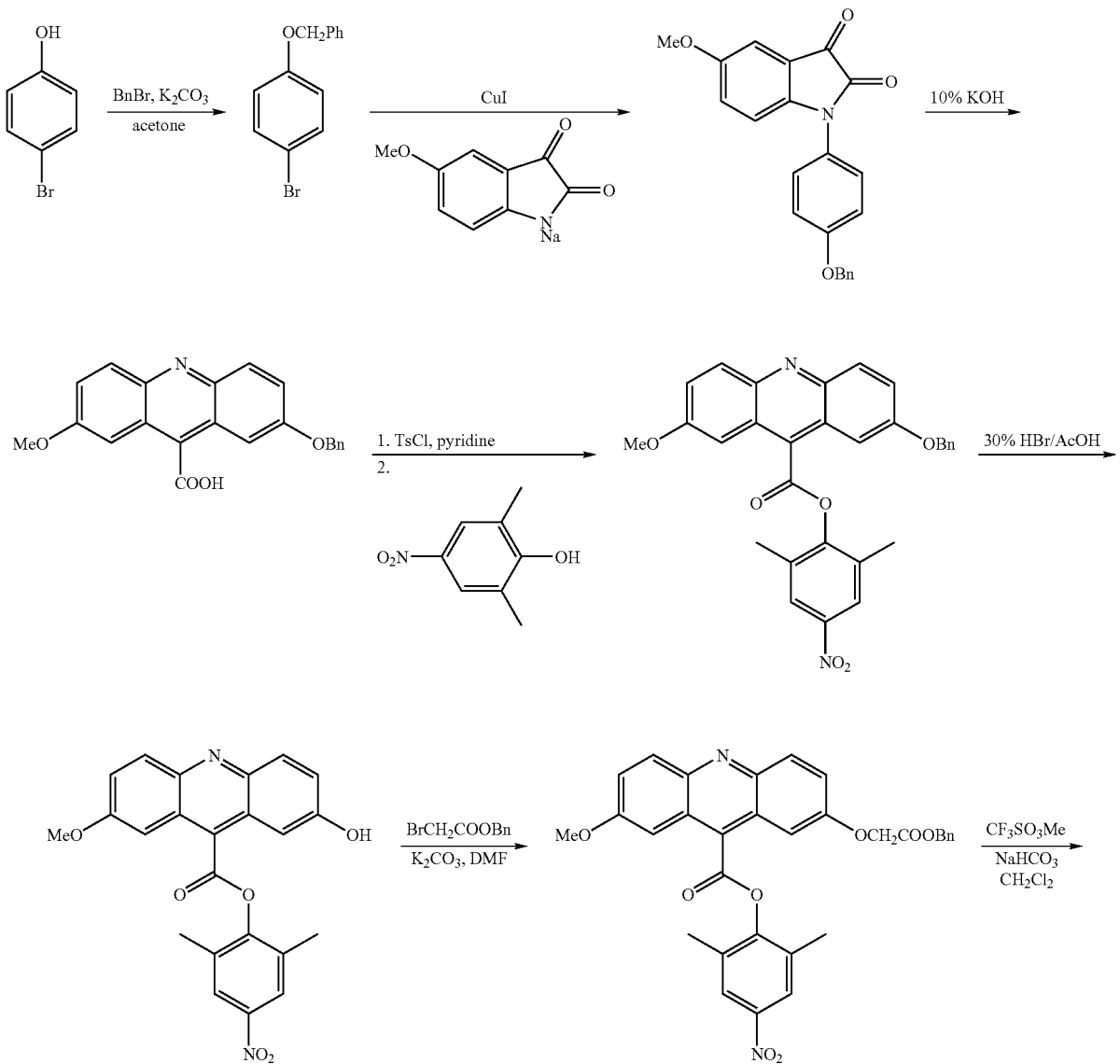

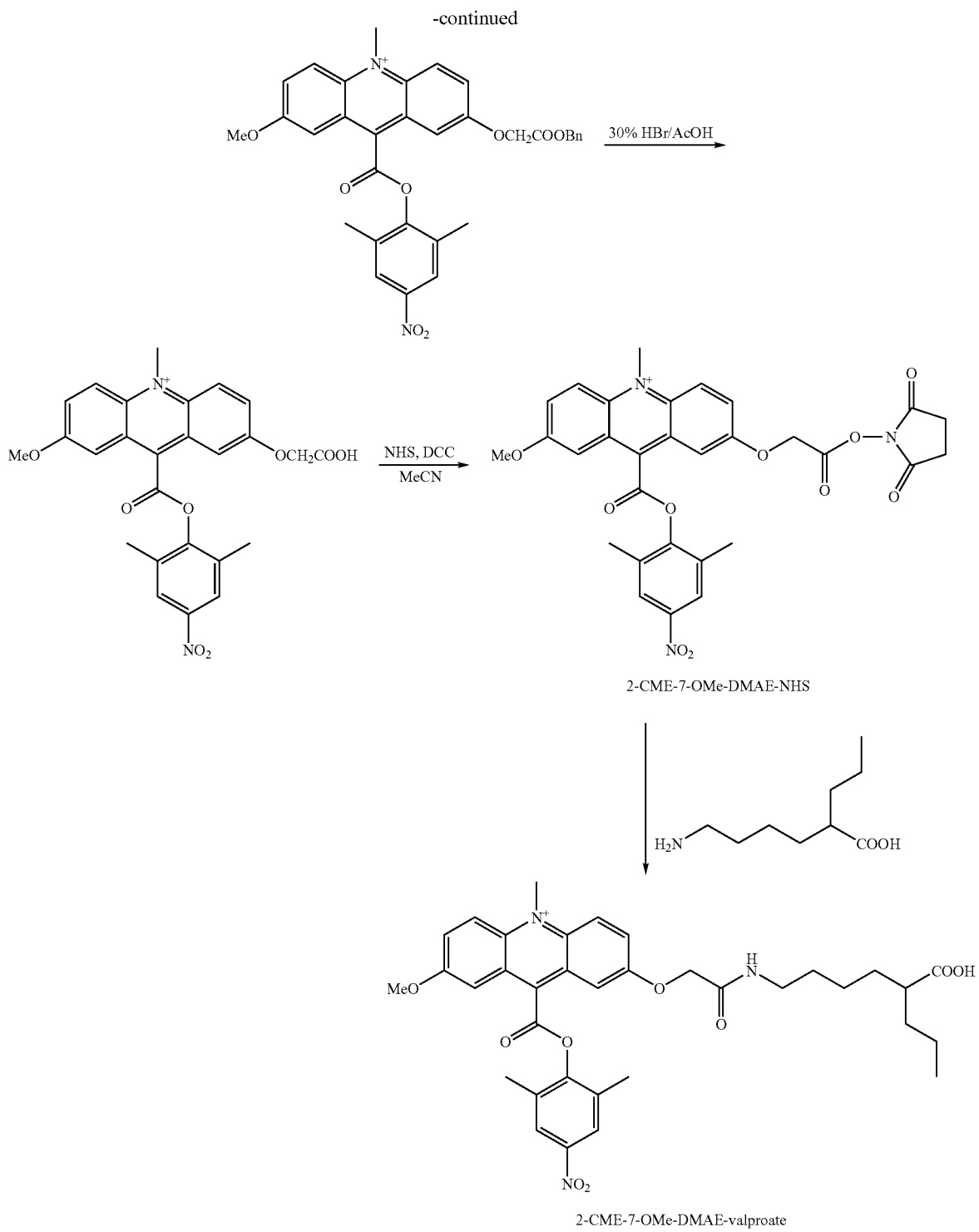

Example 3 pH Titrations of Acridinium Derivatives

This example details how the data in FIGS. 1 and 2 were obtained. FIGS. 1 and 2 illustrate how the acridinium to pseudo-base transition is effected as a function of pH by the placement of methoxy groups on the acridinium ester.

A typical protocol as illustrated for 2,7-dimethoxy-DMAE is as follows. A solution of 2,7-dimethoxy-DMAE (0.5 mg/mL in DMF) was prepared and 20 uL of this solution was diluted with 100 uL of 25 mM phosphate buffer of the appropriate pH and 80 uL of DMF. The solution was allowed to incubate at room temperature for 1.5-2 hours and then the UV spectrum was recorded using a Beckman model DU 7500 spectrophotometer. A 0.1 mL quartz mini-cell was used for the measurements. For each pH, the entire UV spectrum from 220-500 nm was recorded. The intensity of the absorption band of the acridinium chromophore varied with various acridinium derivatives. For 2,7-dimethoxy-DMAE this band was observed at 410 nm whereas for acridinium derivatives, unsubstituted at the acridinium nucleus, this absorption band was observed typically at 363 nm.

Example 4

Synthesis of 3-[9-({(3-carboxypropyl)[(4-methylphenyl) sulfonyl]amino}carbonyl)-10-acridiniumyl]-1-propanesulfonate-valproate Conjugate (NSP-AS-valproate)

NSP-AS-NHS ester (5 mg, 7.32 umoles) and 6-amino-2-propylhexanoic acid (5 mg, 28.9 mmoles) were combined in a 1:1 mixture of DMF and 0.2 M sodium bicarbonate (0.5 mL). The reaction was stirred at room temperature for 2 hours and then for 16 hours at 4° C. HPLC analysis using a 4.6 mm×30 cm C18 column and a 40-minute gradient of 10%->60% MeCN/water (each containing 0.05% TFA) at a flow rate of 1 mL/min and UV detection at 260 nm showed product eluting at 28 minutes. This was purified by preparative HPLC and the HPLC fractions were lyophilized to dryness. Yield=2.2 mg, MALDI-TOF MS 740 obs (739 calc.).

Example 5

(a) Synthesis of Conjugate of 8-carboxypropyl theophylline and 1,6-hexanediamine (theophylline-HD)

8-Carboxypropyltheophylline (40 mg, 150 umoles) in DMF (1.5 mL) was treated with N-hydroxysuccinimide (50 mg, 434 umoles) and DCC (50 mg, 242 µmoles). The reaction was stirred at room temperature for one hour. To this solution, 1,6-hexanediamine (175 mg, 0.15 mmol) was added along with 0.2 M sodium bicarbonate (1.5 mL). The reaction was stirred at room temperature for 16 hours and was purified directly by preparative HPLC on a 20 mm×30 cm C18 column using a 40-minute gradient of 0%->40% MeCN/water (each containing 0.05% TFA) at a flow rate of 16 ml/min and UV detection at 260 nm. The product eluting at 21.5 minutes was collected and the HPLC fractions were concentrated under reduced pressure and further dried under vacuum. Yield=50 mg (91%); MALDI-TOF MS 365 obs. (365.5 calc.).

(b) Synthesis of NSP-AS-HD-theophylline Conjugate

NSP-AS-NHS ester (1.8 mg, 2.82 umoles) and theophylline-HD (10) mg, 28.2 µmoles) were combined in a DMF (0.3 mL). To this solution, 0.2 M sodium bicarbonate (0.3 mL) was added. The reaction was stirred at room temperature for 3 hours. The product was purified on a 10 mm×30 cm C18 column using a 40-minute gradient of 10%->60% MeCN/water (each containing 0.05% TFA) at a flow rate of 2.3 mL/min and UV detection at 260 nm. The HPLC fraction containing product eluted at 24 minutes which was collected and lyophilized to dryness. Yield=1.3 ma (50%); MALDI-TOF MS 932 obs. (933 calc.).

(c) Synthesis of NSP-AS-ED-carbamazepine Conjugate

NSP-AS-NHS ester (2 mg, 2.93 umoles) and carbazepine-ED (10 mg, 35.8 umoles) were combined in DMF (0.3 mL) and 0.2 M sodium bicarbonate (0.3 mL) was added. The reaction was stirred at room temperature for 3 hours. The product was purified as described above for the theophylline conjugate. The product eluting at 33 minutes was collected and the HPLC fractions were lyophilized to dryness. Yield=1 mg (40%); MALDI-TOF MS 846 obs. (846 calc.).

The following reaction equations represent the synthesis of NSP-AS conjugates:

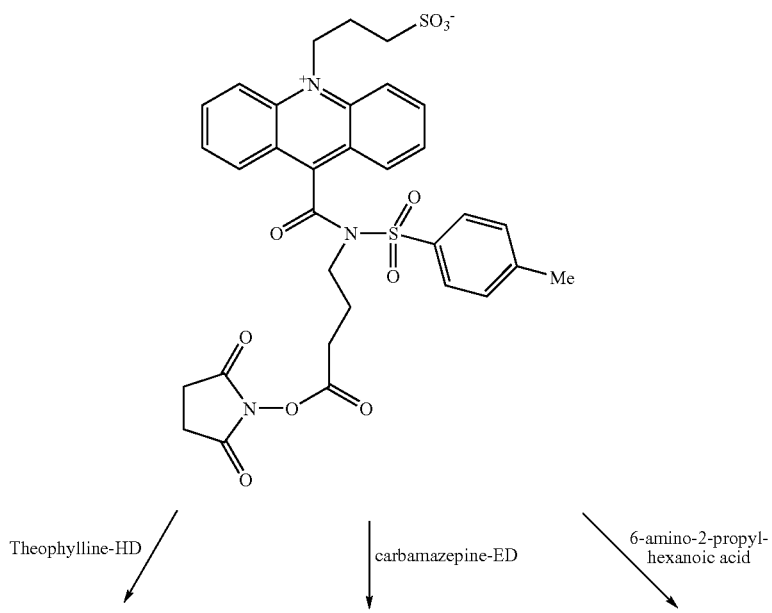

-continued

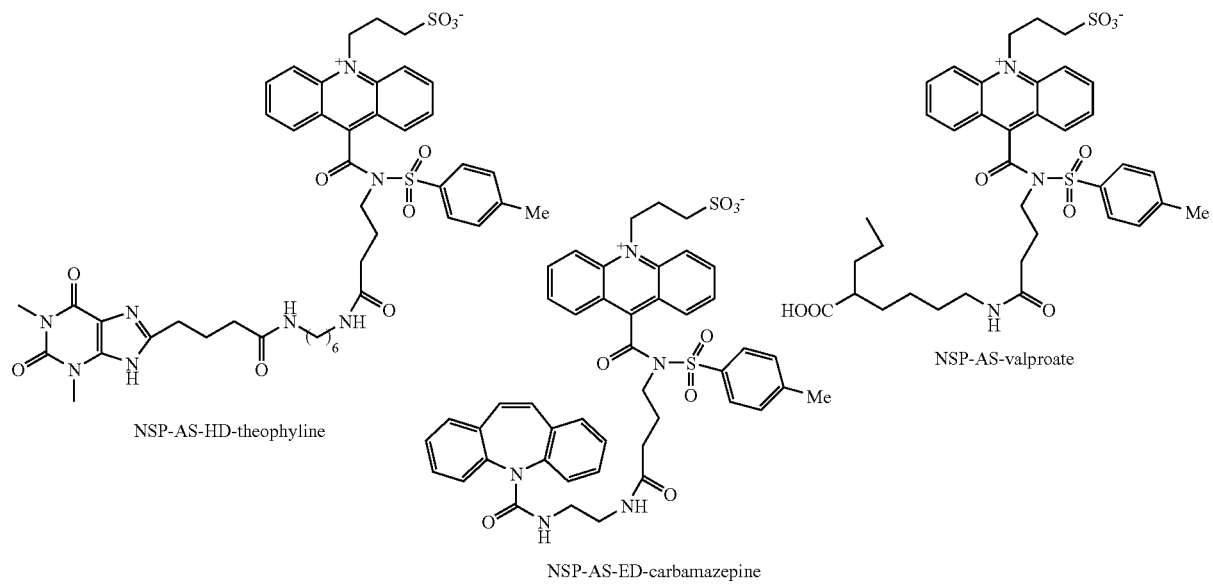

Example 6

(a) Homogeneous Carbamazepine Assay Using 2,7-dimethoxy-DMAE-HD-SA-ED-carbamazepine Conjugate Homogeneous assays were performed in a total volume of 200 uL of 10 mM phosphate containing 150 mM NaCl, 0.05% BSA and 0.01% sodium azide. Carbamazepine standards (0, 4.24, 8.47, 16.9, 33.9, 50.8, 93.2 uM) in human serum were diluted 20-fold into the assay buffer. The final concentrations of carbamazepine in the assay were 0, 0.212, 0.424, 0.845, 1.695, 2.54, 4.66 uM. Assays were run with either 0.02 uM or 0.002 uM tracer with similar results. Binding reactions were initiated with the addition of an anti-carbamazepine, mouse monoclonal antibody to a final concentration of 0.1 uM. After 1 hour at room temperature, chemiluminescence was measured directly (25 uL) on a MLAl (Magic Lite Luminometer, Bayer Diagnostics, no filter) using a modified triggering reagent comprising 3% hydrogen peroxide+0.5% cetyltrimethylammonium chloride (CTAC) in 100 mM $NaHCO_3$. The zero carbamazepine standard and the high carbamazepine standard were differentiated approximately 5-fold in signal in the dose response curve with reasonable assay precision (<6% CV).

Figure 3:
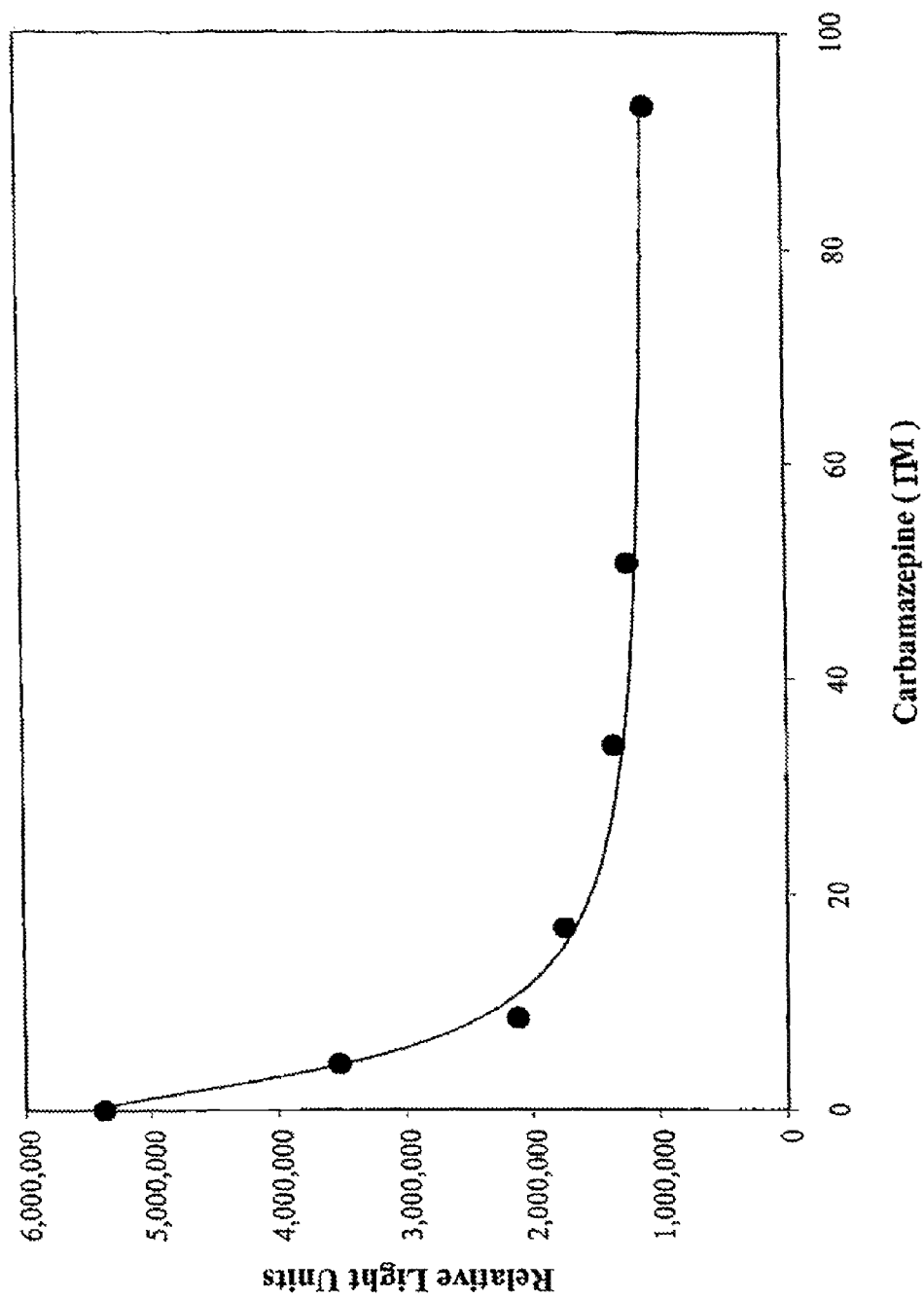

A 4-parameter logistic ("4PL") curve-fitting algorithm was employed to simulate the observed dose response curve. The theoretical dose response curve was virtually superimposable on the observed dose response curve. The data for the homogeneous carbamazepine assay using an acridinium ester tracer appears in Table 3 and has been plotted graphically in FIG. 3.

TABLE 3

| Homogeneous Carbamazepine Assay Using Acridinium Ester Tracer | | |
|---|---|---|
| Carbamazepine, uM | Mean Relative Light Units | % CV |
| 0 | 486107 | 3.56 |
| 4.24 | 333000 | 3.27 |
| 8.47 | 181063 | 4.46 |
| 16.9 | 152220 | 3.14 |
| 33.9 | 125080 | 5.12 |
| 50.8 | 109587 | 3.74 |
| 93.2 | 94320 | 3.93 |

Figure 4:
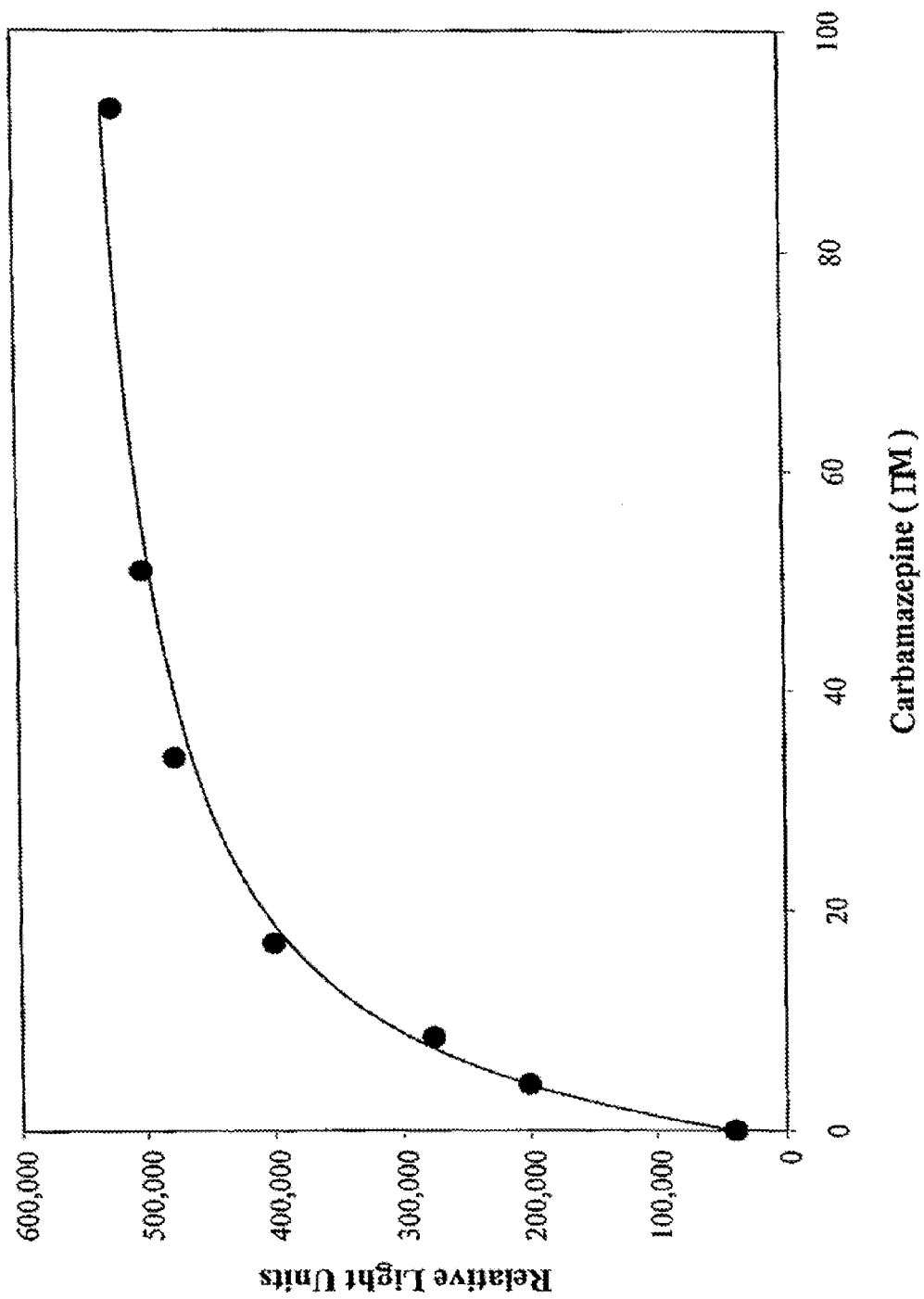

(b) Homogeneous Carbamazepine Assay Using NSP-AS-HD-SA-ED-carbamazepine Conjugate Homogeneous assays were performed in a total volume of 300 uL of 10 mM phosphate containing 150 mM NaCl, 0.05% BSA and 0.01% sodium azide. Carbamazepine standards (0, 4.24, 8.47, 16.9, 33.9, 50.8, 93.2 uM) in human serum were diluted 10-fold into the assay buffer. The final concentrations of carbamazepine in the assay were 0.424, 0.847, 1.69, 3.39, 5.08, 9.32 uM. Assays were run with 0.2 nM tracer. Binding reactions were initiated with the addition of an anti-carbamazepine, mouse monoclonal antibody to a final concentration of 70 nM. After 30 minutes at room temperature, chemiluminescence was measured directly (25 uL) on a MLAl (Magic Lite Luminometer, Bayer Diagnostics, no filter) using a modified triggering reagent comprising 3% hydrogen peroxide+0.5% arquad in 100 mM $NaHCO_3$. The zero Carbamazepine standard and the high Carbamazepine standard were differentiated approximately 13-fold in signal in the dose response curve with reasonable assay precision (<8% CV). The data for the homogeneous carbamazepine assay using an acridinium sulfonamide tracer appears in Table 4 and has been plotted graphically on FIG. 4.

TABLE 4

Homogeneous Carbamazepine Assay Using
Acridinium Sulfonamide Tracer

| Carbamazepine, uM | Mean Relative Light Units | % CV |
|---|---|---|
| 0 | 39775 | 0.59 |
| 4.24 | 201075 | 3.12 |
| 8.47 | 276635 | 7.76 |
| 16.9 | 400335 | 0.04 |
| 33.9 | 477355 | 6.00 |
| 50.8 | 501350 | 3.04 |
| 93.2 | 521020 | 1.53 |

Example 7

Figure 5:
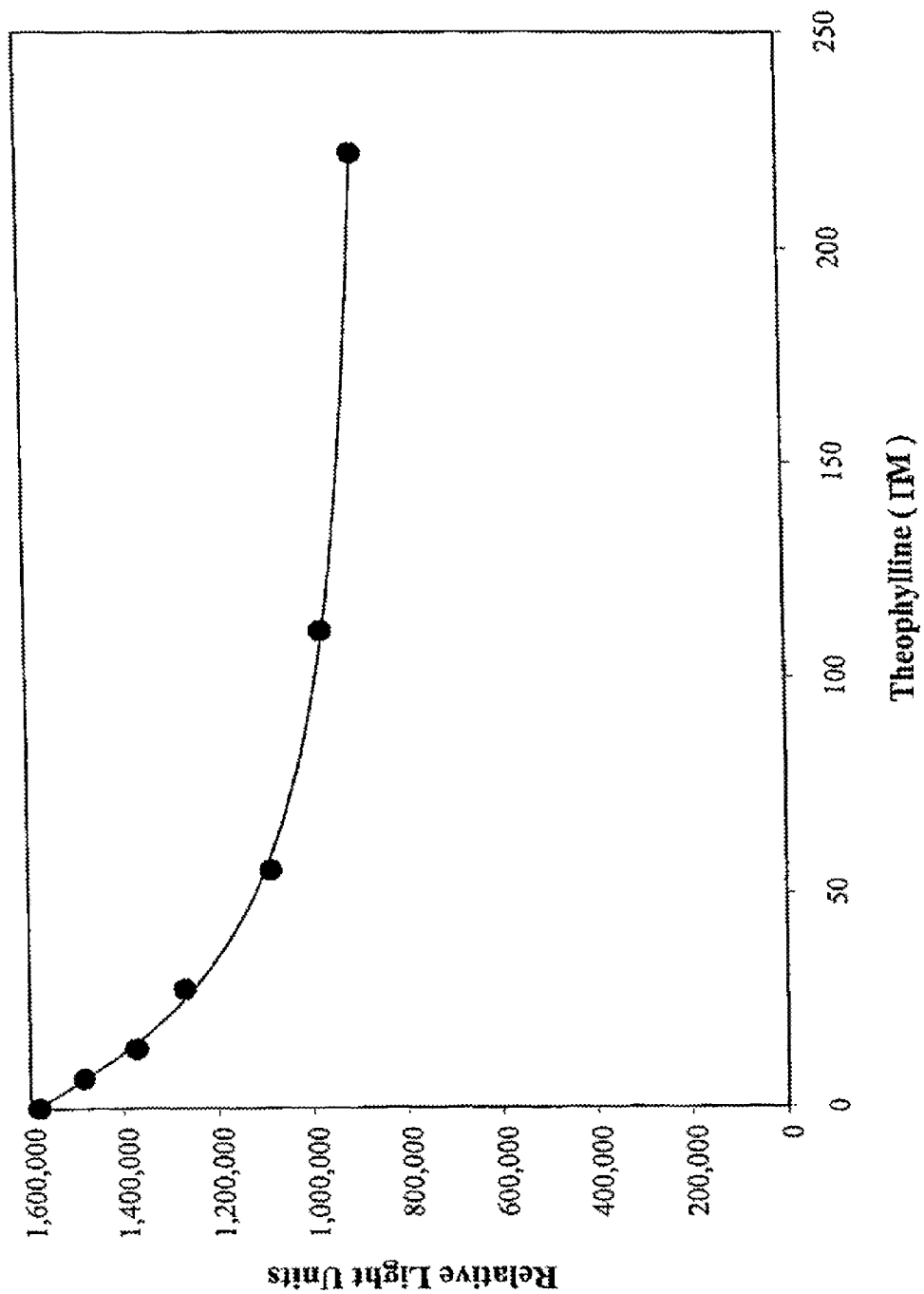

(a) Homogeneous Theophylline Assay Using 2,7-dimethoxy-DMAE-HD-theophylline Conjugate In the homogeneous theophylline assay, reactions were conducted in a total volume of 200 uL of buffer as described in Example 6. Theophylline standards in human serum (0, 6.94, 13.9, 27.7, 55.5, 111, 222 uM) were diluted 10-fold into the reaction to give final theophylline concentrations of 0, 0.694, 1.39, 2.77, 5.55, 11.1 and 22.2 uM. Different concentrations of the tracer and the antibody (anti-theophylline mouse monoclonal) were investigated to determine an optimal concentration of each component which produced the maximum deflection in signal between the zero and high theophylline standard. A maximum enhancement in signal of 2-3-fold was observed by varying the concentration of the tracer from 0.002 to 0.02 uM with an antibody concentration at 0.1 uM. By employing a tracer concentration of 0.002 uM and an antibody concentration of 0.1 uM, the observed dose-response curve was able to distinguish all the theophylline standards. Curve fitting utilizing the 4PL method gave excellent correlation between the theoretical and the observed dose response curves from which the concentration of theophylline in three ACS:180 ligand controls (Bayer Diagnostics) were calculated. The calculated concentrations of theophylline for the three controls were somewhat lower than the indicated concentrations. The data for the homogeneous theophylline assay using an acridinium ester tracer appears in Table 5 and has been plotted graphically in FIG. 5.

TABLE 5

Homogeneous Theophylline Assay Using Acridinium Ester Tracer

| Theophylline, uM | Mean Relative Light Units | % CV |
|---|---|---|
| 0 | 1582490 | 3.51 |
| 6.94 | 1485077 | 3.05 |
| 13.9 | 1371950 | 3.15 |
| 27.7 | 1268183 | 3.41 |
| 55.5 | 1084917 | 4.56 |
| 111 | 973450 | 1.25 |
| 222 | 891833 | 1.10 |

(b) Homogeneous Theophylline Assay Using NSP-AS-HD-theophylline Conjugate

Figure 6:
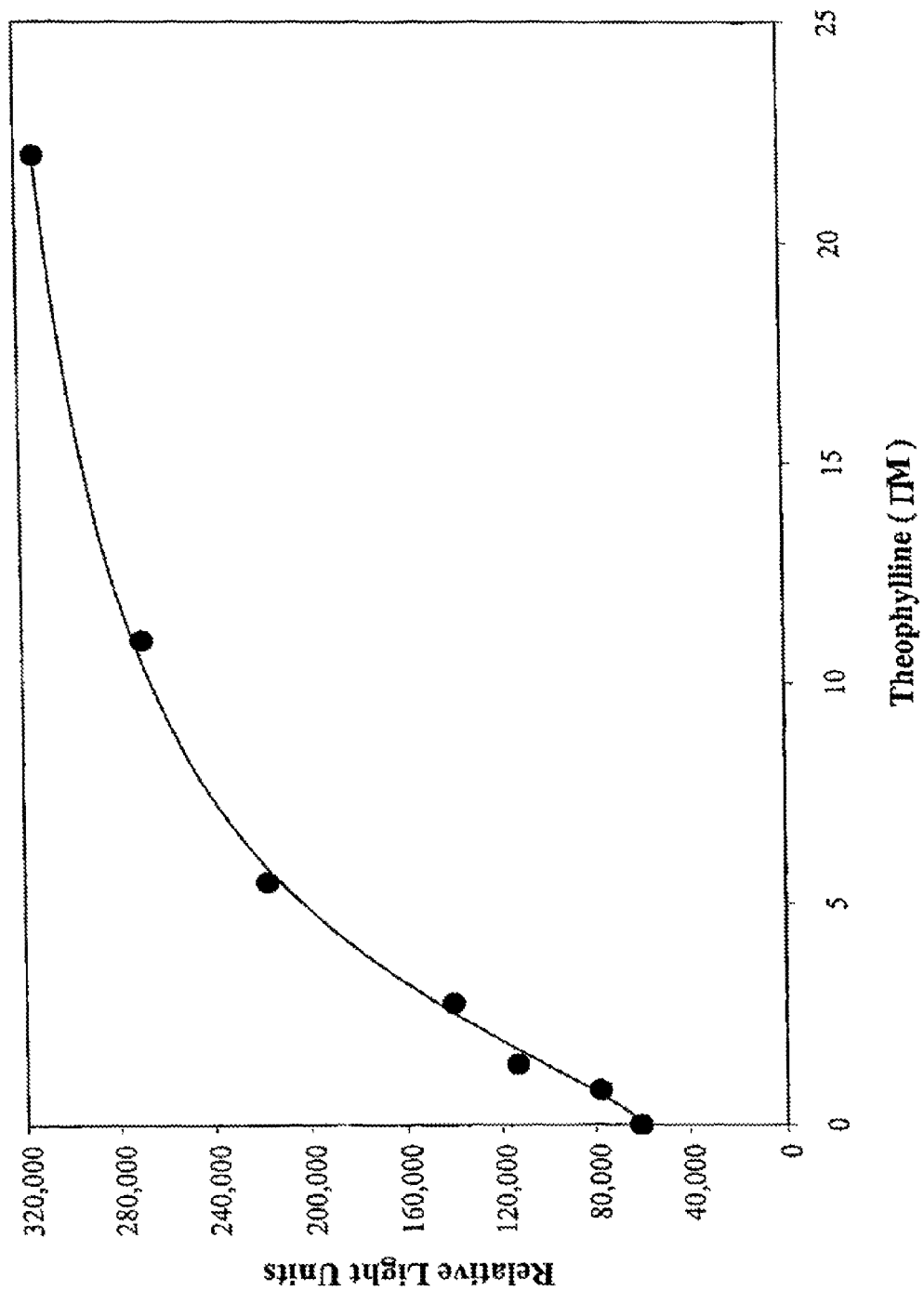

In the homogeneous theophylline assay, reactions were conducted in a total volume of 300 uL of buffer as described in Example 6. Theophylline standards in human serum (0, 6.94, 13.9, 27.7, 55.5, 111, 222 uM) were diluted 10-fold into the reaction to give final theophylline concentrations of 0, 0.694, 1.39, 2.77, 5.55, 11.1 and 22.2 uM. Assays were run with approximately 0.2 mM tracer. Binding reactions were initiated with the addition of an anti-theophylline, mouse monoclonal antibody to a final concentration of 70 nM. After a 30 minute incubation at room temperature chemiluminescence was measured directly (25 uL) on the MLAl (no filter) using the modified triggering reagent. The zero and high theophylline standards were differentiated approximately 5-fold in signal in the dose response curve with reasonable assay precision (<5% CV). The data for the homogeneous theophylline assay using an acridinium sulfonamide tracer appears in Table 6 and has been plotted graphically in FIG. 6.

TABLE 6

Homogeneous Theophylline Assay Using
Acridinium Sulfonamide Tracer

| Theophylline, uM | Mean Relative Light Units | % CV |
|---|---|---|
| 0 | 61270 | 0.53 |
| 6.94 | 77970 | 4.88 |
| 13.9 | 112920 | 2.94 |
| 27.7 | 139890 | 2.47 |
| 55.5 | 216630 | 1.78 |
| 111 | 268835 | 2.45 |
| 222 | 312575 | 1.74 |

Example 8

(a) Homogeneous Valproate Assay Using 2,7-dimethoxy-DMAE-valproate Conjugate

Figure 7:
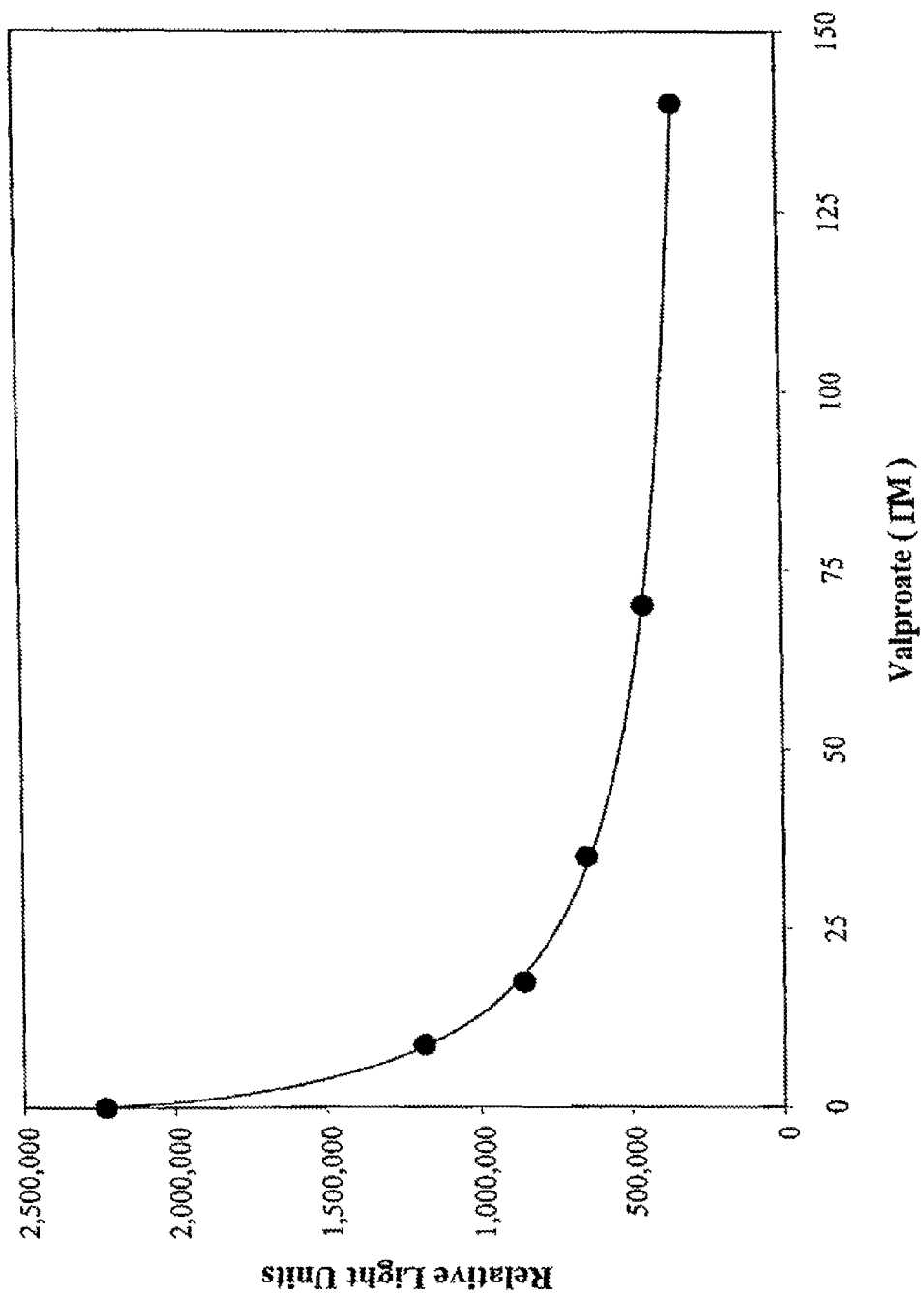

The assay was conducted in 100 uL of buffer as described in Example 6. Valproate standards (0, 87.5, 175, 350, 700 and 1400 uM) in human serum were diluted 10-fold into the assay buffer. A tracer concentration of 0.2 uM was employed and the concentration of the anti-valproate, mouse monoclonal was 1 uM. Reactions were initiated by the addition of the antibody and after incubation at room temperature for 1 hour, the reactions were diluted 100-fold and measured as indicated earlier. The zero and high valproate standard were differentiated by ~10-fold in signal. Again assay precision was good and all the valproate standards could clearly be distinguished from one another. The data for the homogeneous valproate assay using an acridinium ester tracer appears in Table 7 and has been plotted graphically in FIG. 7.

TABLE 7

Homogeneous Valproate Assay Using Acridinium Ester Tracer

| Valproate, uM | Mean Relative Light Units | % CV |
|---|---|---|
| 0 | 2226627 | 2.94 |
| 87.5 | 1179153 | 4.36 |
| 175 | 853790 | 3.97 |
| 350 | 645213 | 3.45 |
| 700 | 451783 | 1.35 |
| 1400 | 337943 | 5.24 |

(b) Homogeneous Valproate Assay Using NSP-AS-Valproate Conjugate

Figure 8:
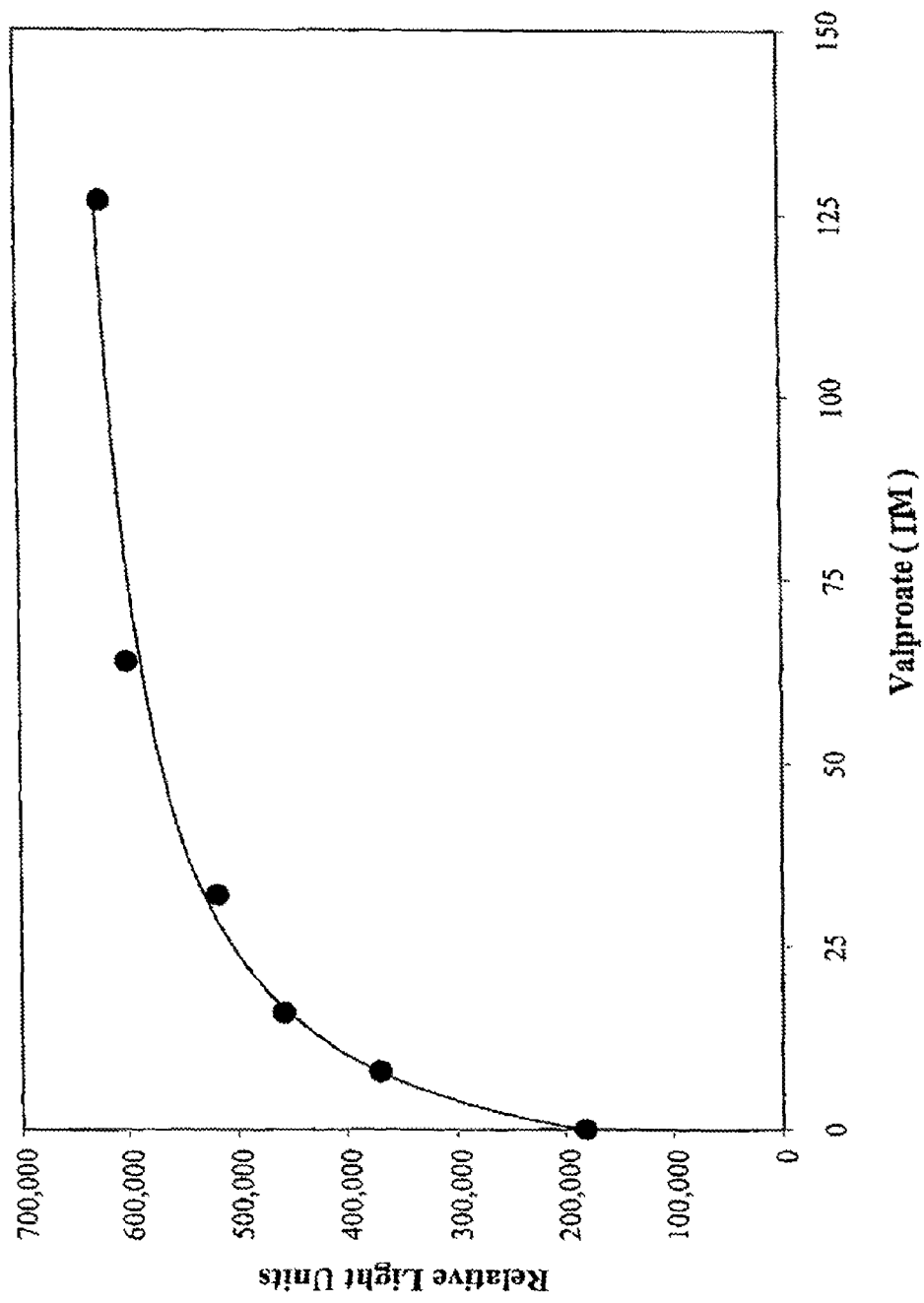

The assay was conducted in 300 uL of buffer as described in Example 6. Valproate standards (0, 87.5, 175, 350, 700 and 1400 uM) in human serum were diluted 10-fold in to the assay buffer to give final valproate concentrations of 0, 8.75, 17.5, 35, 70 and 140 uM. A tracer concentration of approximately 0.2 nM was employed and the concentration of the anti-valproate, mouse monoclonal was 70 nM. Reactions were initiated by the addition of the antibody and after a 30 minute incubation at room temperature chemiluminescence was measured directly (25 uL) on the MLAl (no filter) using the modified triggering reagent. The zero and high valproate standards were differentiated approximately 3.4-fold in signal in the dose response curve with reasonable assay precision (8% CV). The data for the homogeneous valproate assay using an acridinium sulfonamide tracer appears in Table 8 and has been plotted graphically in FIG. 8.

TABLE 8

Homogeneous Valproate Assay Using Acridinium Sulfonamide Tracer

| Valproate, uM | Mean Relative Light Units | % CV |
|---|---|---|
| 0 | 182265 | 1.02 |
| 87.5 | 370895 | 6.61 |
| 175 | 458255 | 0.55 |
| 350 | 518490 | 8.10 |
| 700 | 600600 | 3.41 |
| 1400 | 628925 | 4.26 |

Example 9

(a) Synthesis of Conjugate of Dabsyl Chloride and Ethylene Diamine (dabsyl-ED)

Dabsyl chloride (25 mg, 0.077 mol, Aldrich) was added to ethylene diamine (36 ul, 7 equivalents) in dichloromethane (2 mL). After 10-15 minutes, TLC (25% ethyl acetate in hexanes) indicated no starting material. The reaction was concentrated under reduced pressure and the residue was dissolved in MeCN. HPLC analysis using a 4.6 mm×30 cm C18 column and a 30-minute gradient of 10%->100% MeCN/water (each containing 0.05% TFA) showed a single product eluting at 13.5 minutes. The product was purified by preparative HPLC and the HPLC fractions were concentrated to a small volume by rotary evaporation and then lyophilized to dryness. Yield=35 mg (80%); MALDI-TOF MS 348.3 obs. (347.4 calc.).

(b) Synthesis of dabsyl-ED-glutarate-NHS ester

Dabsyl-ED (15 mg, 26.1 umoles) in MeCN (3 mL) was treated with N,N-diisopropylethylamine (9.2 uL, 2 equivalents) followed by glutaric anhydride (9 mg, 3 equivalents). After 2 hours at room temperature, HPLC analysis using a 4.6 mm×30 cm C18 column and a 30-minute gradient of 10%->70% MeCN/water (each containing 0.05% TFA) at a flow rate of 1 mL/min and UV detection at 260 nm showed complete conversion with the product eluting at 18 minutes (starting material elutes at 16 minutes). To this solution N-hydroxysuccinimide (15 mg, 5 equivalents) was added followed by DCC (27 mg, 5 equivalents). The reaction was stirred at room temperature. After one hour, HPLC analysis indicated ~70% conversion. Additional DCC (13.5 mg, 2.5 equivalents) was added and the reaction was continued for another hour. The reaction was then filtered through glass wool and the product was purified by preparative HPLC. The HPLC fractions were lyophilized to dryness. Yield=14.8 mg (85%).

(c) Synthesis of Anti-Valproate-dabsyl Conjugate

An anti-valproate monoclonal antibody (0.5 mg, 0.45 mL of 1.1 mg/mL stock in PBS pH 7.4) was diluted with 0.1 M sodium bicarbonate (0.45 mL). This solution was treated with a 50 uL of a DMF solution of dabsyl-ED-glutarate-NHS ester (2 mg/mL in DMF). The labeling reaction was carried out for 2-3 hours at room temperature and then the conjugate was isolated by gel-filtration chromatography on Sephadex G25 using 10 mM phosphate pH 7 as eluent. The extent of dabsyl incorporation was determined by MALDI-TOF MS which indicated ~9 dabsyls per protein. The conjugate was stored at 4° C.

Figure 9:
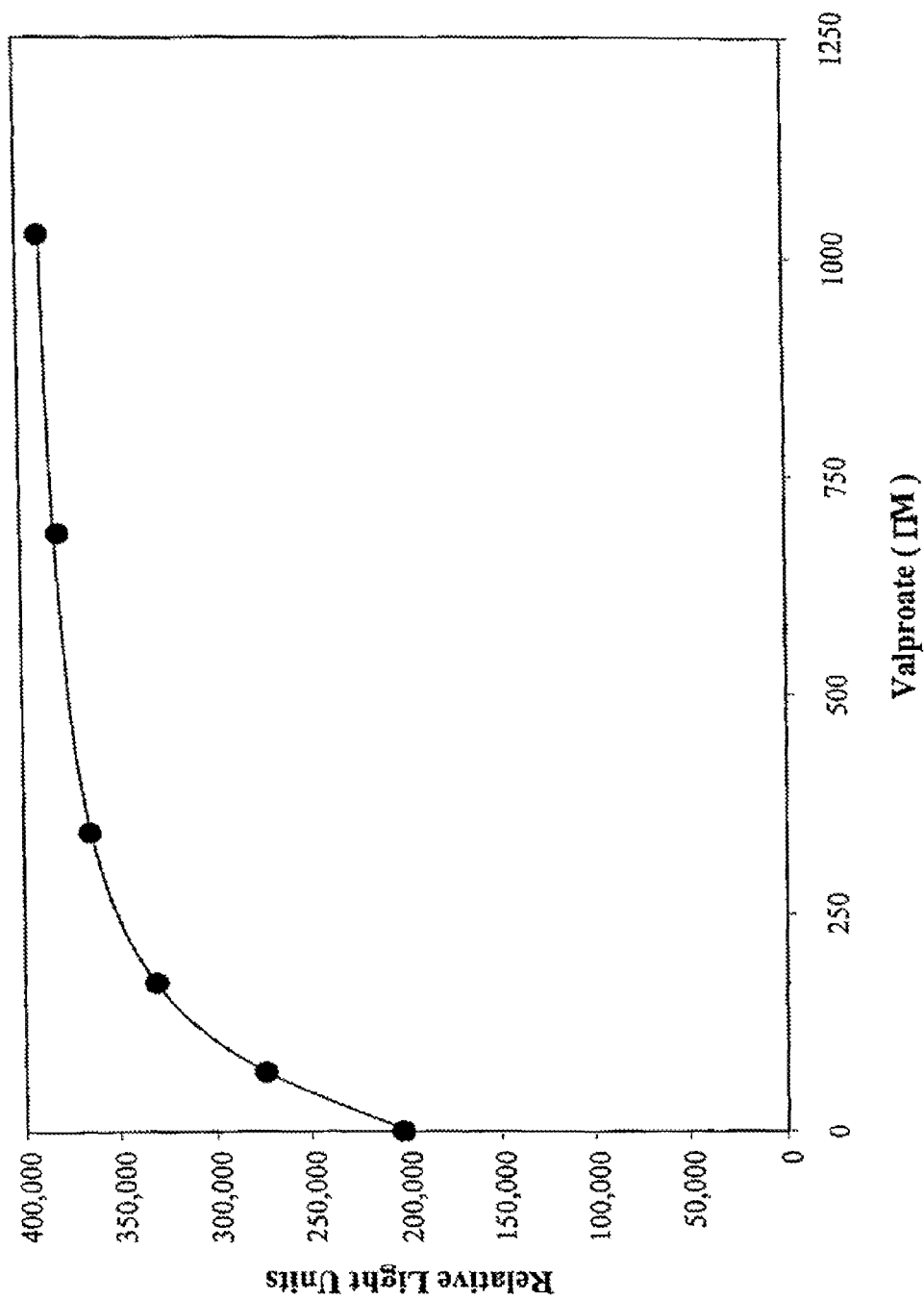

(d) Homogeneous Valproate Assay Using Dabsyl-Labeled Anti-Valproate Antibody and 2-CME-7-methoxy-DMAE-valproate Reactions were run in 0.2 mL of buffer as described in Example 6. Valproate standards in sheep serum were employed at concentrations of 0, 10, 25, 50, 100 and 150 ug/mL which correspond to 0, 68.5, 171, 342.5, 685, 1027.5 uM. The tracer was employed at a concentration of 1.29 nM. The dabsyl-labeled antibody was added last at a final concentration of 0.4 uM. The reactions were incubated at room temperature for one hour and were then read directly as described in Example 6. The data obtained for the homogeneous valproate assay using quenching was plotted graphically in FIG. 9.

Example 10

Conjugates for CL Resonance Energy Transfer (a) Biotin Conjugate of Naphthofluorescein
A solution of naphthofluorescein NHS ester (2.3 mg) in DMF (0.25 ml) was mixed with a solution of biotin-jeffamine (conjugate of biotin triethylene glycol diamine, 15 mg) in DMF (0.25 ml) and carbonate buffer (0.10 M, pH 8.5, 0.30 ml). After this mixture was stirred at room temperature overnight, solvents were removed under vacuum, and the residue was taken up in $CH_3CN$/water for HPLC purification (C-18 reversed phase chromatography). The isolated product was identified by MALDI-TOF mass spectrometry. (833.2 calc., 833.5 obs.)

(b) Biotin Conjugate of Acridinium Analog
Biotin-jeffamine (2.0 mg) and 2-CME-7-methoxy-DMAE NHS ester (0.5 mg) were dissolved in 0.50 ml of DMF, and the solution was stirred at room temperature over a period of three hours. After the solvents were removed under vacuum, the desired product was isolated from C-18 reversed phase chromatography and confirmed by MALDI-TOF mass spectrometry. (847.3 calc., 848.2 obs.)

(c) Preparation of anti-HCG(beta)-naphthofluorescein
0.30 ml of mouse monoclonal anti-HCG-beta (Bayer, #10244590, 10.2 mg/ml) in acetate buffer (10 mM, pH 5.5) was passed through a G-25 column (1 cm×15 cm) for buffer exchange, eluted with phosphate buffer (0.10 M, pH 8.0), and 2.0 ml of protein was collected with total of 2.8 mg of antibody. One third of that collected sample was mixed with naphthofluorescein-NHS in DMF (0.10 ml, 1.0 mg/1.5 ml, 20 eq. total). After two hours, the reaction mixture was washed with PBS (20 mM, pH 7.4, 0.15 M NaCl, 0.05% $NaN_3$) through CentriCon 10 (0.66 ml, 0.60 mg/ml). MALDI-TOF of the product indicated 4.5 dyes were incorporated into one antibody.

(d) Preparation of anti-HCG(whole)-2-CME-7-methoxy-DMAE 0.90 ml of anti-HCG (whole) at 3.5 mg/ml in 0.15 M phosphate-0.1% $NaN_3$, pH 7.4 was passed through a G-25 column (1 cm×15 cm) eluted with phosphate buffer (0.10 M, pH 8.0), and the collected fractions were pooled and concentrated through CentriCon 10 to a volume of 0.90 ml at 2.3 mg/ml. One third of this sample was incubated with a sample of 2-CME-7-methoxy-DMAE NHS ester in DMF (0.075 ml, 0.50 mg/0.70 ml, 20 eq.) for two hours. Purification through G-25 column and concentration through CentriCon 10 gave a product 0.21 mg (0.52 mg/ml) in PBS buffer (20 mM, pH 7.4, 0.15 M NaCl, 0.05% $NaN_3$). MALDI-TOF analysis showed 1.3 labels were attached to the antibody.

Example 11

Titration of Avidin and Biotin-AE with Biotin-JfNpFL in Homogeneous CL Resonance Energy Transfer Reactions Binding reactions (300 uL) were assembled in BSA-PBS (0.1% BSA-10 mM potassium phosphate-0.15 M NaCl-0.05% sodium azide, pH 8) as shown in Table 9. Biotin-jeffamine-naphtofluorescein, abbreviated as "biotin-Jf-Np-FL, 100 uL" at varying levels and biotin-hexaethylene glycol-2-CME-7-methoxy-DMAE, abbreviated as "biotin-AE, 100 uL" were premixed and the competitive binding reactions (6-14) were initiated by addition of 1 uM neutravidin (Pierce) or streptavidin (100 uL, Sigma) and mixing, followed by 30 minutes incubation at 37° C. Control reactions (1-5) received the reagents shown and were brought to 300 uL with BSA-PBS. The data appears in Table 9. The data for each reaction appears as a numbered row in Table 9, with the first row of data representing reaction 1, the second row representing reaction 2 and so forth.

CL was measured at 4° C. on a MLAl with red sensitive PMT-tube (Hamamatsu R7228) and 2 filters (Corion cut-off filters, to read >650 nm) using a single injection of 300 uL of 1% peroxide-0.5% CTAC-0.1 M sodium bicarbonate-0.05% sodium azide, pH 8.3. Net RLUs per 5 seconds shown are the counts with 2100 or 2300 RLU for background for avidin alone subtracted. BiotinNpFL alone also gave this low background and by itself was not enhanced by either avidin. See data for reactions 4 and 5 in Table 9. Neutravidin alone enhanced biotin-AE CL ~4-fold, while streptavidin alone decreased it ~3-fold. See data for reactions 6 and 3 in Table 9. The inclusion of biotin-JfNpFL gave a dose dependent further increase in CL. See data reactions 7-14 vs reaction 6 in Table 9. The range of biotin-JfNpFL discernable with biotin AE and streptavidin was ~2 to 3 orders of magnitude, with a lower detection limit of <0.005 uM in the 100 uL sample. See FIG. 10 which represents a plot of 'CL RET from Biotin-AE to Biotin-jfNpFL in a Streptavidin Complex'.

Figure 10:
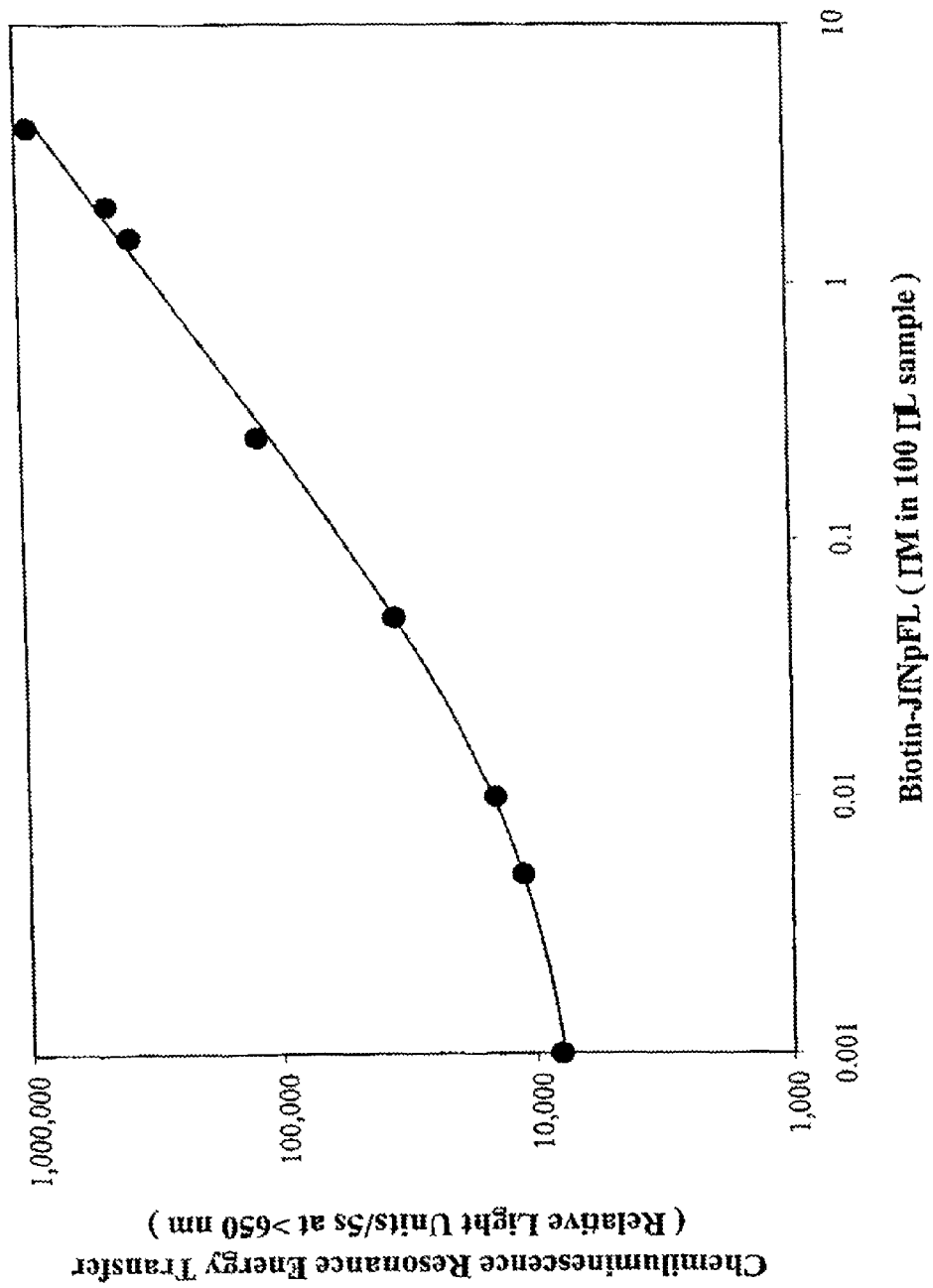

As shown in FIG. 10, at optimum concentrations the RET signal with streptavidin increased to a maximum of 110-fold and with neutravidin by up to 10-fold. These results suggest that a sandwich assay up to 3 log dynamic range may be possible if the RET binding complex can be reduced in size to that of the biotin:avidin complex.

The binding of biotin-AE alone to avidin caused a modulation in the chemiluminescence signal produced. Compare the data for reaction 3 with that for reaction 6 in Table 9. The signal of 22,585 increased to 81,710 with neutravidin and decreased to 8,110 with streptavidin. Interestingly, neutravidin enhanced chemiluminescence (480 nm), while streptavidin decreased it. Thus, site specific chemical modification of antibodies may be useful to modulate the signal produced by bound CL label. Consequently, in this example the amount of chemiluminescence RET (>650 nm), when biotin-NpFL at varying levels in binding reactions competed with biotin-AE for avidins, also depended on the avidin species.

TABLE 9

CL Resonance Energy Transfer in a Biotin-AE:Avidin:Biotin-JfNpFL Complex

| | 0.025 uM Biotin-AE (uL) | 100 uL Biot-JfNpFL (uM) | 1 uM Avidin | BSA-PBS pH 8 (uL) | Neutravidin RLU/5s | Streptavidin RLU/5 s |
|---|---|---|---|---|---|---|
| 1. | 0 | 0 | 0 | 300 | 2,230 | 2,230 |
| 2. | 0 | 0 | 100 | 200 | 2,075 | 2,340 |
| 3. | 100 | 0 | 0 | 200 | 22,585 | 22,585 |
| 4. | 0 | 1.000 | 0 | 200 | 2,185 | 2,265 |
| 5. | 0 | 1.000 | 100 | 100 | 2,080 | 2,370 |

| | | | | | Net RLU/5 s | Signal/BG | Net RLU/5 s | Signal/BG |
|---|---|---|---|---|---|---|---|---|
| 6. | 100 | 0.000 | 100 | | 81,710 | 1.00 | 8,110 | 1.00 |
| 7. | 100 | 0.005 | 100 | | 97,085 | 1.18 | 11,275 | 1.39 |
| 8. | 100 | 0.010 | 100 | | 103,550 | 1.27 | 14,430 | 1.78 |
| 9. | 100 | 0.050 | 100 | | 193,420 | 2.36 | 34,910 | 4.30 |
| 10. | 100 | 0.250 | 100 | | 409,350 | 5.10 | 117,130 | 14.44 |
| 11. | 100 | 1.000 | 100 | | 456,335 | 5.59 | 367,075 | 45.26 |
| 12. | 100 | 1.500 | 100 | | 848,860 | 10.39 | 357,275 | 44.05 |
| 13. | 100 | 2.000 | 100 | | 851,365 | 10.42 | 436,045 | 53.77 |
| 14. | 100 | 4.000 | 100 | | 283,835 | 3.47 | 893,085 | 110.12 |

Example 12

Homogeneous Sequential Saturation Assay for Biotin Via CL Energy Transfer with Biotin-AE, Biotin-Jf-Np-FL and Neutravidin Biotin (100 uL) at the indicated concentration and 100 uL of 1 uM neutravidin were mixed and incubated for 1 hr a 20° C. (Table 10). Then a solution of 25 nM biotin-AE and 250 nM biotin-Jf-Np-FL was added, mixed and followed by 30 min incubation at 37° C. Finally, readout was performed on the MLAl as above. All background controls were low (reactions 1-4). Net RLUs are counts minus the 3285 RLU background for neutravidin alone. Initial binding of biotin reduced the amount of labeled biotins bound in the next step, thereby reducing the RET perceptably above 2.5 uM biotin in a dose dependent manner.

Free biotin was allowed to compete with fixed levels of biotin-AE, biotin-NpFL and neutravidin. As shown in Table 10, biotin bound to neutravidin in place of some of the labeled conjugates reduced the otherwise enhanced energy transfer.

TABLE 10

Homogeneous Assay for Biotin via CL RET with Biotin-HEG-AE, Biotin-JfNpFL and Neutravidin

| Rxn. | Incubation: for 60 min. at 20° C. | | | 30 min. at 37° C. | |
|---|---|---|---|---|---|
| | 100 uL Biotin (uM) | 1 uM Neutravidin (uL) | BSA/PBS pH 8 (uL) | 25 nM Biotin-AE 250 nM Biot-JfNpFL (uL) | CL SIGNAL RLU/5 s |
| 1 | 0 | 0 | 300 | 0 | 3,180 |
| 2 | 0 | 100 | 200 | 0 | 3,285 |
| 3 | 10 uM | 0 | 200 | 0 | 3,480 |
| 4 | 10 uM | 100 | 100 | 0 | 3,675 |
| 5 | 0 | 0 | 200 | 100 | 22,265 |
| | | | | | Net RLU/5 s (%) |
| 6 | 0.0 | 100 | 100 | 100 | 411,995  100.0 |
| 7 | 0.1 | 100 | 100 | 100 | 389,205  94.5 |
| 8 | 0.5 | 100 | 100 | 100 | 423,255  100.5 |
| 9 | 1.0 | 100 | 100 | 100 | 465,025  112.9 |
| 10 | 2.5 | 100 | 100 | 100 | 384,720  93.4 |
| 11 | 5.0 | 100 | 100 | 100 | 30,040  7.3 |
| 12 | 7.5 | 100 | 100 | 100 | 23,710  5.8 |
| 13 | 10.0 | 100 | 100 | 100 | 21,200  5.1 |
| 14 | 20.0 | 100 | 100 | 100 | 19,145  4.6 |

Example 13

(a) Homogeneous Immunoassay for HCG Via CL Resonance Energy Transfer

This example details a homogeneous assay for HCG where one antibody is labeled with an acridinium ester (2-CME-7-methoxy-DMAE) while the second antibody is labeled with a fluorescent dye (naphthofluorescein)

Competitive binding reactions (300 uL) were assembled in BSA-PBS. Anti-HCG (wholo) (7504MR)-(2-CME-7-methoxy-DMAE)$_{1.3}$ was premixed to 10.4 ug/mL with anti-HCG beta (102445901)-(naphthofluorescein)$_{4.5}$ to 12.0 ug/mL final. Then HCG standards (200 uL) at the varying concentration indicated in Table 2 were added to 100 uL of the premix per tubes (quadruplicates, each standard), sealed, and followed by a mix and 1 hr incubation in a 37° C. water bath. Finally 2 tubes for each standard were measured in the MLAl at 4° C. by road out with the single reagent (pH 8.3) CL initiation as above. Five minutes later the other two tubes were read out by on the same instrument, using the single CL reagent readout where the signal reached maximum at 5000 mIU/mL HCG with a 2.7-fold increase over that at 0 HCG and then declined gradually.

What is claimed is:

1. A homogenous assay method for detection or quantitation of an analyte in a sample, comprising the steps of:
   (a) providing a conjugate comprising a chemiluminescent acridinium sulfonamide compound attached to an analyte or analyte analog, wherein the sulfonamide of said acridinium sulfonamide compound is linked to the 9 position of the acridinium nucleus through a carbonyl group;
   (b) adding a predetermined amount of said conjugate to a sample containing an unknown concentration of said analyte;
   (c) adding an antibody specific to said analyte to form a binding complex with either said analyte or said conjugate;
   (d) incubating the solution of said binding complex;
   (e) triggering the chemiluminescence of said binding complex reaction mixture by adding peroxide in a pH range of about 6 to 10 to cause light emission without the addition of a strong acid or a strong base;
   (f) measuring the amount of light emission; and
   (g) calculating the concentration of said analyte by comparing the amount of light emitted from the reaction mixture with a standard dose response curve which relates the amount of light emitted to a known concentration of said analyte.

2. The method of claim 1, wherein said conjugate is formed by reacting said analyte with a chemiluminescent acridinium sulfonamide compound having the following structure:

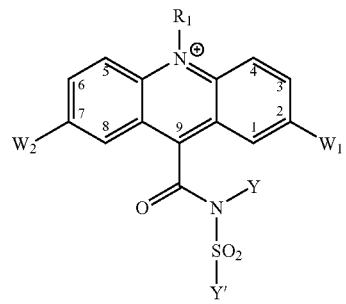

wherein $R_1$ is an alkyl, alkenyl, alkynyl or aralkyl, each of which may contain up to 20 heteroatoms; or a sulfopropyl or sulfobutyl group;

Y and Y' are independently selected from branched or straight-chain alkyl, aryl, or heterocyclic ring system, containing up to 20 heteroatoms;

$W_1$ and $W_2$ are the same or different and are selected H or an electron donating group of the form OR*, OH, SR*, SH, $NH_2$, or NR'R''; wherein R*, R' and R'' can be the same or different, and are selected from the group consisting of alkyl, alkenyl, alkynyl, aryl, and aralkyl, each containing up to 20 heteroatoms.

3. The method of claim 2, wherein said chemiluminescent acridinium sulfonamide compound has the following structure:

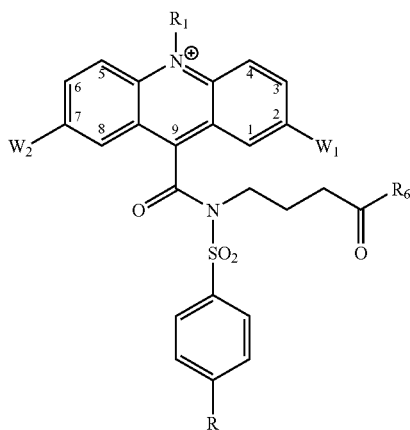

where,

R$_6$ is a group —R$_9$-R$_{10}$, where R$_9$ is not required or is branched or straight-chained alkyl, substituted or unsubstituted aryl or aralkyl, each comprising up to 20 heteroatoms, and R$_{10}$ is a leaving group or an electrophilic functional group attached with a leaving group selected from the group consisting of

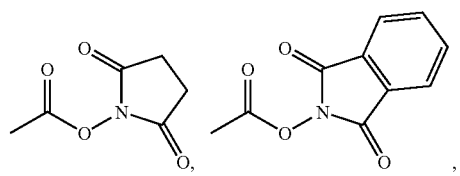

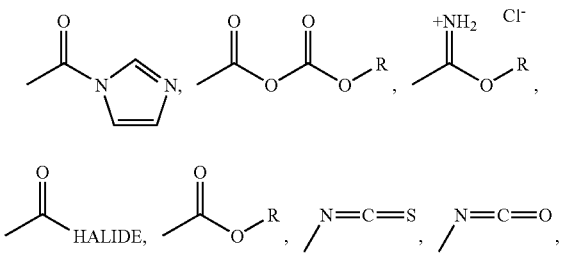

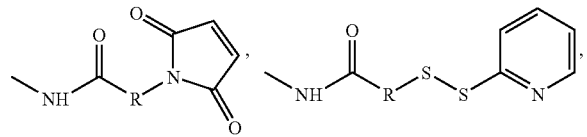

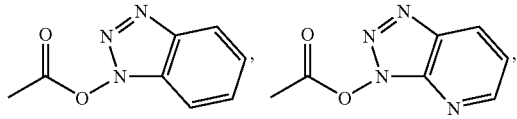

—SO$_2$Cl, —N$_3$, —N$_2$$^+$Cl$^-$, halide, and a carboxylic acid, and R is selected from the group consisting of alkyl, alkenyl, alkynyl, aryl, and aralkyl, each optionally comprising up to 20 heteroatoms.

4. The method of claim 1, wherein said conjugate is formed by reacting said analyte with a chemiluminescent acridinium sulfonamide compound having the following structure:

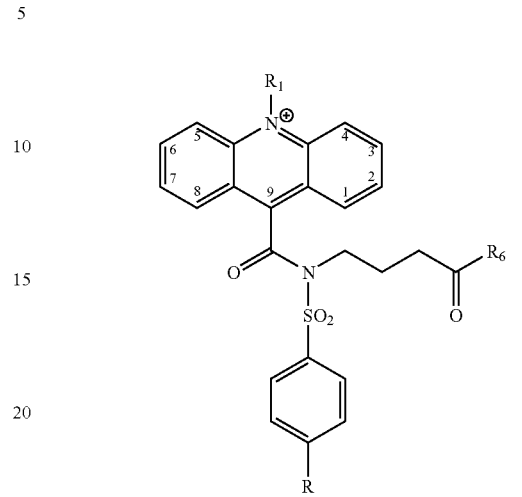

where,

R$_1$ is an alkyl, alkenyl, alkynyl or aralkyl, each of which may contain up to 20 heteroatoms; or a sulfopropyl or sulfobutyl group;

R$_6$ is a group —R$_9$-R$_{10}$, where R$_9$ is not required or is branched or straight-chained alkyl, substituted or unsubstituted aryl or aralkyl, each comprising up to 20 heteroatoms, and R$_{10}$ is a leaving group or an electrophilic functional group attached with a leaving group selected from the group consisting of:

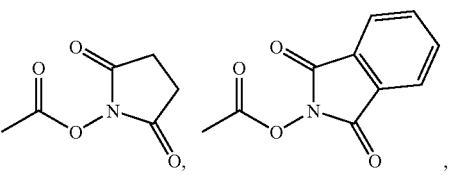

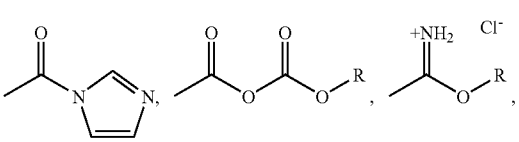

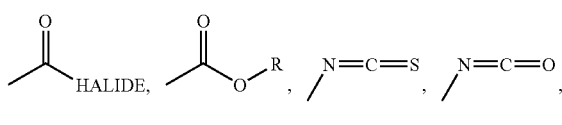

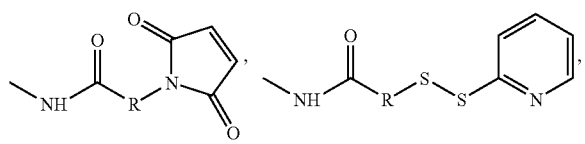

-continued

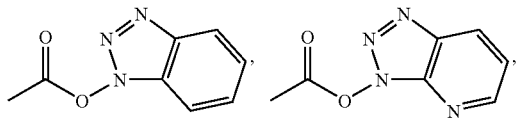

—SO₂Cl, —N₃, —N₂⁺Cl⁻, halide, and a carboxylic acid,

R is selected from the group consisting of alkyl, alkenyl, alkynyl, aryl, and aralkyl, each optionally comprising up to 20 heteroatoms.

5. The method of claim 1, wherein said conjugate is formed by reacting said analyte with a chemiluminescent acridinium sulfonamide compound having the following structure:

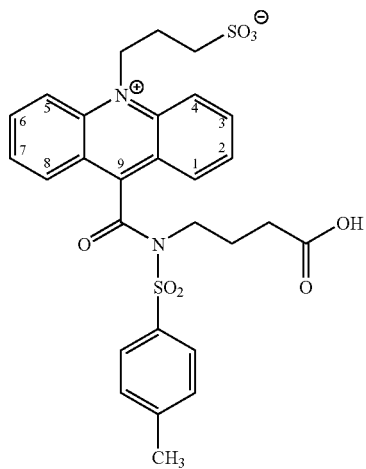

6. The method of claim 1, wherein said conjugate is formed by reacting said analyte with a chemiluminescent acridinium sulfonamide compound having the following structure:

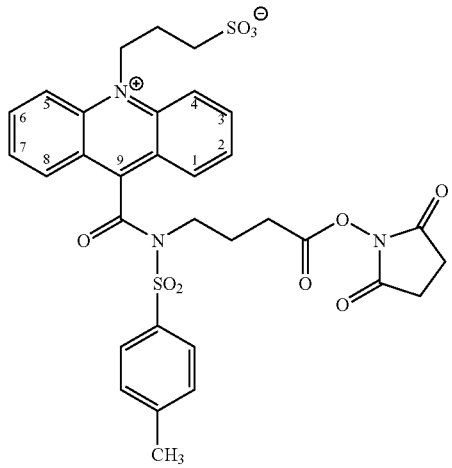

7. The method of claim 1, wherein the analyte of interest is a small molecule selected from the group consisting of steroids, therapeutic drugs, vitamins, hormones and peptides.

8. The method of claim 1, wherein the peroxide is hydrogen peroxide, sodium peroxide, or bivalent peroxide salts.

9. The method of claim 1, wherein said chemiluminescent acridinium sulfonamide compound comprises an electron donating functional group attached to the C2 position on the acridinium nucleus.

10. The method of claim 1, wherein said chemiluminescent acridinium sulfonamide compound comprises electron donating functional groups attached to the C2 and C7 positions on the acridinium nucleus.

11. The method of claim 1, wherein said conjugate of said acridinium sulfonamide compound exhibits a decreased chemiluminescent efficiency when in said binding complex than when free in solution.

* * * * *